US006149910A

United States Patent [19]

De Leys et al.

[11] Patent Number: 6,149,910
[45] Date of Patent: Nov. 21, 2000

[54] PEPTIDES FOR THE DETECTION OF HIV-1 GROUP O

[75] Inventors: Robert De Leys, Three Bridges; Jian Zheng, Raritan, both of N.J.

[73] Assignee: Ortho-Clinical Diagnostics, Inc., Rochester, N.Y.

[21] Appl. No.: 09/433,428

[22] Filed: Nov. 4, 1999

[51] Int. Cl.[7] .......................... A61K 39/21; A61K 39/00; A61K 39/38; A61K 39/12; A61K 38/00

[52] U.S. Cl. .................................... 424/188.1; 424/184.1; 424/185.1; 424/186.1; 424/204.1; 424/208.1; 530/324; 530/300

[58] Field of Search .............................. 424/184.1, 185.1, 424/186.1, 188.1, 204.1, 208.1; 530/324, 300

*Primary Examiner*—Jeffrey Stucker
*Assistant Examiner*—Brett Nelson
*Attorney, Agent, or Firm*—Stacey B. Antar

[57] ABSTRACT

This invention relates to peptides and their preparation. The peptides each have a sequence that corresponds to the immunodominant region of the HIV-1 group O gp41 envelope protein. The sequence is characterized in that it does not correspond to any known naturally occurring group O sequence or variant. Furthermore, the peptide binds anti-HIV-1 group O antibodies. There are several uses for the peptides, including the detection of antibodies produced in response to HIV-1 group O infection. The peptides may also be incorporated in mosaics and expressed recombinantly.

3 Claims, 10 Drawing Sheets

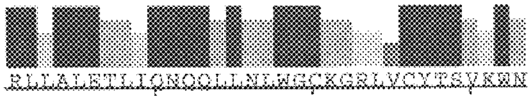

| | | | | |
|---|---|---|---|---|
| | | | +Majority | |
| | | RLLALETLIQNQQLLNLWGCKGRLVCYTSVKWN | Majority | |
| | | 10 20 30 | | |
| SEQ ID NO:1 | 1 | RLLALETLLQNQQLLSLWGCKGKLVCYTSVKWN | ANT70 | |
| SEQ ID NO:2 | 1 | RLQALETLIQNQQRLNLWGCKGKLICYTSVKWN | MVP5180 | |
| SEQ ID NO:3 | 1 | RLLALETFIQNQQLLNLWGCKNRLICYTSVKWN | VAU | |
| SEQ ID NO:4 | 1 | RLLALETLIQNQQLLNLWGCKGRLVCYTSVKWN | BCF09 | |
| SEQ ID NO:5 | 1 | RLLALETLIQNQQLLNLWGCKGRLICYTSVKWN | BCF12 | |
| SEQ ID NO:6 | 1 | RLLALETLIQNQQLLNSWGCKGRLVCYTSVEWN | BCF13 | |
| SEQ ID NO:7 | 1 | RLLALETLIQNQQLLNSWGCKGRQVCYTSVKWN | BCF14 | |
| SEQ ID NO:8 | 1 | RLLALETLIQNQQLLNLWGCKGRLICYTSVQWN | 686 | |
| SEQ ID NO:9 | 1 | RLLALETLMQNQQLLNLWGCKGRILCYTSVKWN | 1515 | |
| SEQ ID NO:10 | 1 | RLLALETLIQNQQLLNLWGCKGRIVCYTSVRWN | 1516 | |
| SEQ ID NO:11 | 1 | RLLALETLIQNQQLLNLWGCKGKIVCYTSVEWN | 193Ha | |
| SEQ ID NO:12 | 1 | RLLALETLMQNQQLLNLWGCKGKLICYTSVRWN | ABT063 | |
| SEQ ID NO:13 | 1 | RLQALETLIQNQQRLDLWGCKGRIICYTSVKWN | ABT1123 | |
| SEQ ID NO:14 | 1 | RLLALETFIQNQQLLNLWGCKGRLICYTSVKWN | ABT124 | |
| SEQ ID NO:15 | 1 | RLLALETLIQNQQLLNLWGCKGRLVCYTSVKWN | ABT2156 | |
| SEQ ID NO:16 | 1 | RLLALETLIQNQQLLNSWGCQGKLVCYTSVIWN | CDC1897 | |
| SEQ ID NO:17 | 1 | RLQALETLMQNQQLLNLWGCKGKSICYTSVKWN | CDC7755 | |
| SEQ ID NO:18 | 1 | RLLALETFVQNQQLLNLWGCKGRIVCYTSVKWN | D47-2d | |
| SEQ ID NO:19 | 1 | RLLALETLMQNQQLLNLWGCRGKAICYTSVQWN | DUR | |
| SEQ ID NO:20 | 1 | RLQALETLIQNQQLLSLWGCKGRLVCYTSVKWH | POC | |
| SEQ ID NO:21 | 1 | RLLALETLIQNQQLLNLWGCKGRLLCYTSVKWN | FAN | |
| SEQ ID NO:22 | 1 | RLLALETFIQNQQLLNLWGCKGKLICYTSVEWN | HCYT2c. | |
| SEQ ID NO:23 | 1 | RLQALETLMQNQQRLDLWGCKGRLICYTSVKWN | HLD28 | |
| SEQ ID NO:24 | 1 | RLQALEPLIQNQQRLSLWGCKGRIICYTSAKWN | LOB | |
| SEQ ID NO:25 | 1 | RLLALETLIQNQQLLNSWGCKGRLVCYTSVKWN | MAN | |
| SEQ ID NO:26 | 1 | RLVALETLVQNQQLLNLWGCKGRLTCYTSVKWN | NAN | |
| SEQ ID NO:27 | 1 | RLLALETLIQNQQLLNLWGCKGRLLCYTSVKWN | NKO | |
| SEQ ID NO:28 | 1 | RLLALETFIQNQQLLNLWGCKGQLVCYTSVKWN | Nr42 | |
| SEQ ID NO:29 | 1 | RLLALETFIQNQQLLNLWGCKGRLICYTSVKWN | PE41 | |
| SEQ ID NO:30 | 1 | RLLALETLIQNQQLLNSWGCKGRIVCYTSVKWN | ESS | |

Figure 1. Alignment of HIV-1 group O immunodominant region amino acid sequences

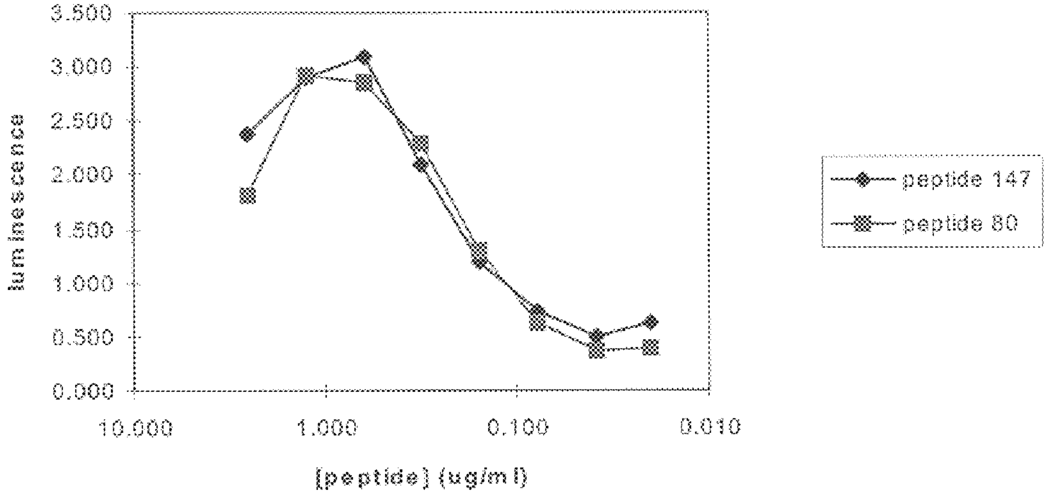
Figure 2. Recognition of peptides 147 and 80 by an HIV-1 group O sample.

SEQ ID NO:70
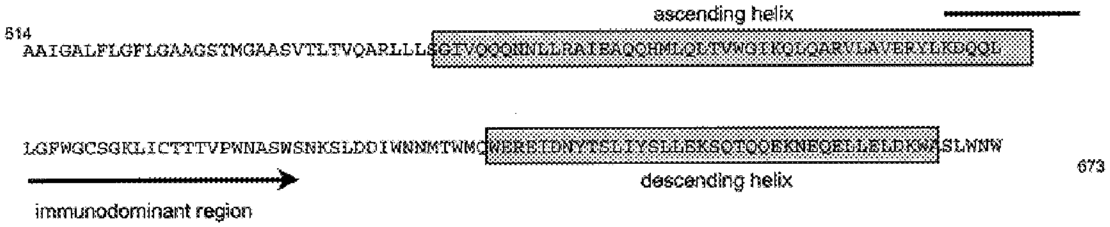
Figure 3. Ectodomain of gp41 (MN isolate)

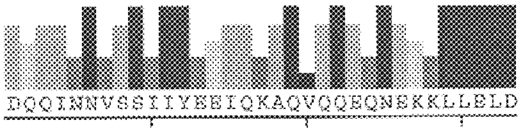

| | | | | |
|---|---|---|---|---|
| | | DQQINNVSSIIYEEIQKAQVQQEQNEKKLLELD | | Majority |
| | | 10 20 30 | | |
| SEQ ID NO:31 | 1 | EREIDNYTSLIYSLLEKSQTQQEKNEQELLELD | | MN |
| SEQ ID NO:32 | 1 | DRQISNISSTIYEEIQKAQVQQEQNEKKLLELD | | ANT70 |
| SEQ ID NO:33 | 1 | DQHINNVSSIIYDEIQAAQDQQEKNVKALLELD | | MVP5180 |
| SEQ ID NO:34 | 1 | DQQINNVSSFIYEKIQEAQEQQEKNEKELLELD | | VAU |
| SEQ ID NO:35 | 1 | DQQIDNISSTIYDEIQKAQVQQEQNEQKLLELD | | 686 |
| SEQ ID NO:36 | 1 | DQQINNISSIIYGEIQKAQVQQEENEKKLLELD | | 1515 |
| SEQ ID NO:37 | 1 | DQQINNISSIIYGEIQKAQVQQEHNEKKLLELD | | 1516 |
| SEQ ID NO:38 | 1 | DQQVNNVSSFIYDKIQEAQEQQEENERALLELD | | CDC7755 |
| SEQ ID NO:39 | 1 | DQQISNVSSIIYEEIQKAQEQQEQNEKKLLELD | | D47-2d |
| SEQ ID NO:40 | 1 | DQQIANVSSFIYDQIQEAQERQDKNEKTLLELD | | DUR |
| SEQ ID NO:41 | 1 | DQQIDNVSSTIYEEILKAQIQQEQNEKKLLELD | | ESS |
| SEQ ID NO:42 | 1 | DREIDNISSYIYEKIQEAQDQQENNERELLELD | | HCYT2c |
| SEQ ID NO:43 | 1 | DKQISNISSIIYDEIQTAQDQQERNVKALLELD | | HLD28 |
| SEQ ID NO:44 | 1 | DQQVNNVSSIIYEEIQRAQVQQEQNEKRLLELD | | Nr42 |
| SEQ ID NO:45 | 1 | DQQIDNVSSIIYEEIQKAQGQQEQNEKKLLELD | | PE41 |

Figure 4. Alignment of MN (type B) and group O gp41 sequences in the region of the descending helix

Primers used in the experiment:

| | | |
|---|---|---|
| SEQ ID NO:46 | FA: | 5'-ATTTTGGAAGCCCAGGATCAACAAGAGGAGAACGTTCGTGAGTTGCTGGAGCTAGATAAATGG |
| SEQ ID NO:47 | FB: | 5'-AGCAAGTTAACAATGTTTCTTCTATTATTTATGATAAGATTTTGGAAGCCCAGGATCA |
| SEQ ID NO:48 | RA: | 5'-CAAGAATTCAGACGCTGTTGGTTTTGCATCAGAGTCTCCAGAGCCTGTAGGCGAGCTCGGAGCTG |
| SEQ ID NO:49 | RB: | 5'-GGGCACTAGTATAACAAATAATACGACCCTTACAACCCCAAGAATTCAGACGCTGT |
| SEQ ID NO:50 | RC: | 5'-CCAGATATCCTCCAGAGACTTATTAGACCAAGAAGCATGCCAACGGGCACTAGTATAACAAA |
| SEQ ID NO:51 | RD: | 5'-ACATTGTTAACTTGCTGGTCCCATTGCATCCAGGTCATGTTATCCCAGATATCCTCCAGAGA |
| SEQ ID NO:52 | U19: | 5'-GTTTTCCCAGTCACGACGT |
| SEQ ID NO:53 | R20: | 5'-CAGCTATGACCATGATTACG |
| SEQ ID NO:54 | R33-3: | 5'-ACCGGAATTCCGATTTCCTTGGGTT |
| SEQ ID NO:55 | F33-2: | 5'-CATAAAGCTTGTCCCAGAAGTTCC |
| SEQ ID NO:56 | F33-6: | 5'-GCCACTGCAGCCAGACTATTATTGTC |

Figure 5d. Nucleotide sequences of the primers used in Figures a - c.

SEQ ID NO:57

DHFR

MRGSGIMVRPLNSIVAVSQNMGIGKNGDLPWPPLRNEFKYFQRMTTTSSVEGKQNLVIMGRKTWFSIPEKNRPLKDRINI

VLSRELKEPPRGAHFLAKSLDDALRLIEQPELASKVDMVWIVGGSSVYQEAMNQPGHLRLFVTRIMQEFESDTFFPEIDL

GKYKLLPEYPGVLSEVQEEKGIKYKFEVYEKKGSRSAKLLLSGIVQQQNNLLRAIEAQQHMLQLTAWGIKQLRARLQALE

TLMQNQQRLNSWGCKGRIICYTSARWHASWSNKSLEDIWDNMTWMQWDQQVNNVSSIIYDKILEAQDQQEENVRELLELD group O　　　　group O

KWASLWNWFDITNWLWYIKIFIMIVGGLVGLRIVFAVLSIVNRVRQGYSPLSLQTRPPVPRGPDRPEGIEEEGGERDRDT

SGRLVHGFLAIIWVDLGEEQKLISEEDLNSAVDHHHHHH

*myc*　　　　(His)$_6$

Figure 6a. Amino acid sequence of DHFR-hENV-MH

SEQ ID NO:58

DHFR

MRGSGIMVRPLNSIVAVSQNMGIGKNGDLPWPPLRNEFKYFQRMTTTSSVEGKQNLVIMGRKTWFSIPEKNRPLKDRINI

VLSRELKEPPRGAHFLAKSLDDALRLIEQPELASKVDMVWIVGGSSVYQEAMNQPGHLRLFVTRIMQEFESDTFFPEIDL

GKYKLLPEYPGVLSEVQEEKGIKYKFEVYEKKGSKSARILLSGIVQQQNNLLRAIEAQQHMLQLTAWGIKQLRARLQALE

TLMQNQQRLNSWGCKGRIICYTSARWHASWSNKSLEDIWDNMTWMQWDQQVNNVSSIIYDKILEAQDQQEENVRELLELD group O group O

KWASLWNWFDITNWLWYIKIFIMIVGPEQKLISEEDLNSAVDHHHHHH

*myc* (His)$_6$

Figure 6b. Sequence of DHFR-hES-MH

SEQUENCE LISTING

```
<160> NUMBER OF SEQ ID NOS:  70

<210> SEQ ID NO 1
<211> LENGTH: 33
<212> TYPE: PRT
<213> ORGANISM: Human immunodeficiency virus type 1

<400> SEQUENCE: 1

Arg Leu Leu Ala Leu Glu Thr Leu Leu Gln Asn Gln Gln Leu Leu Ser
  1               5                  10                  15

Leu Trp Gly Cys Lys Gly Lys Leu Val Cys Tyr Thr Ser Val Lys Trp
             20                  25                  30

Asn


<210> SEQ ID NO 2
<211> LENGTH: 33
<212> TYPE: PRT
<213> ORGANISM: Human immunodeficiency virus type 1

<400> SEQUENCE: 2

Arg Leu Gln Ala Leu Glu Thr Leu Ile Gln Asn Gln Gln Arg Leu Asn
  1               5                  10                  15

Leu Trp Gly Cys Lys Gly Lys Leu Ile Cys Tyr Thr Ser Val Lys Trp
             20                  25                  30

Asn


<210> SEQ ID NO 3
<211> LENGTH: 33
<212> TYPE: PRT
<213> ORGANISM: Human immunodeficiency virus type 1

<400> SEQUENCE: 3

Arg Leu Leu Ala Leu Glu Thr Phe Ile Gln Asn Gln Gln Leu Leu Asn
  1               5                  10                  15

Leu Trp Gly Cys Lys Asn Arg Leu Ile Cys Tyr Thr Ser Val Lys Trp
             20                  25                  30

Asn


<210> SEQ ID NO 4
<211> LENGTH: 33
<212> TYPE: PRT
<213> ORGANISM: Human immunodeficiency virus type 1

<400> SEQUENCE: 4

Arg Leu Leu Ala Leu Glu Thr Leu Ile Gln Asn Gln Gln Leu Leu Asn
  1               5                  10                  15

Leu Trp Gly Cys Lys Gly Arg Leu Val Cys Tyr Thr Ser Val Lys Trp
             20                  25                  30

Asn


<210> SEQ ID NO 5
```

-continued

<211> LENGTH: 33
<212> TYPE: PRT
<213> ORGANISM: Human immunodeficiency virus type 1

<400> SEQUENCE: 5

```
Arg Leu Leu Ala Leu Glu Thr Leu Ile Gln Asn Gln Gln Leu Leu Asn
  1               5                  10                  15

Leu Trp Gly Cys Lys Gly Arg Leu Ile Cys Tyr Thr Ser Val Lys Trp
             20                  25                  30

Asn
```

<210> SEQ ID NO 6
<211> LENGTH: 33
<212> TYPE: PRT
<213> ORGANISM: Human immunodeficiency virus type 1

<400> SEQUENCE: 6

```
Arg Leu Leu Ala Leu Glu Thr Leu Ile Gln Asn Gln Gln Leu Leu Asn
  1               5                  10                  15

Ser Trp Gly Cys Lys Gly Arg Leu Val Cys Tyr Thr Ser Val Glu Trp
             20                  25                  30

Asn
```

<210> SEQ ID NO 7
<211> LENGTH: 33
<212> TYPE: PRT
<213> ORGANISM: Human immunodeficiency virus type 1

<400> SEQUENCE: 7

```
Arg Leu Leu Ala Leu Glu Thr Leu Ile Gln Asn Gln Gln Leu Leu Asn
  1               5                  10                  15

Ser Trp Gly Cys Lys Gly Arg Gln Val Cys Tyr Thr Ser Val Lys Trp
             20                  25                  30

Asn
```

<210> SEQ ID NO 8
<211> LENGTH: 33
<212> TYPE: PRT
<213> ORGANISM: Human immunodeficiency virus type 1

<400> SEQUENCE: 8

```
Arg Leu Leu Ala Leu Glu Thr Leu Ile Gln Asn Gln Gln Leu Leu Asn
  1               5                  10                  15

Leu Trp Gly Cys Lys Gly Arg Leu Ile Cys Tyr Thr Ser Val Gln Trp
             20                  25                  30

Asn
```

<210> SEQ ID NO 9
<211> LENGTH: 33
<212> TYPE: PRT
<213> ORGANISM: Human immunodeficiency virus type 1

<400> SEQUENCE: 9

```
Arg Leu Leu Ala Leu Glu Thr Leu Met Gln Asn Gln Gln Leu Leu Asn
  1               5                  10                  15

Leu Trp Gly Cys Lys Gly Arg Ile Leu Cys Tyr Thr Ser Val Lys Trp
             20                  25                  30

Asn
```

-continued

<210> SEQ ID NO 10
<211> LENGTH: 33
<212> TYPE: PRT
<213> ORGANISM: Human immunodeficiency virus type 1

<400> SEQUENCE: 10

```
Arg Leu Leu Ala Leu Glu Thr Leu Ile Gln Asn Gln Gln Leu Leu Asn
  1               5                  10                  15

Leu Trp Gly Cys Lys Gly Arg Ile Val Cys Tyr Thr Ser Val Arg Trp
             20                  25                  30

Asn
```

<210> SEQ ID NO 11
<211> LENGTH: 33
<212> TYPE: PRT
<213> ORGANISM: Human immunodeficiency virus type 1

<400> SEQUENCE: 11

```
Arg Leu Leu Ala Leu Glu Thr Leu Ile Gln Asn Gln Gln Leu Leu Asn
  1               5                  10                  15

Leu Trp Gly Cys Lys Gly Lys Ile Val Cys Tyr Thr Ser Val Glu Trp
             20                  25                  30

Asn
```

<210> SEQ ID NO 12
<211> LENGTH: 33
<212> TYPE: PRT
<213> ORGANISM: Human immunodeficiency virus type 1

<400> SEQUENCE: 12

```
Arg Leu Leu Ala Leu Glu Thr Leu Met Gln Asn Gln Gln Leu Leu Asn
  1               5                  10                  15

Leu Trp Gly Cys Lys Gly Lys Leu Ile Cys Tyr Thr Ser Val Arg Trp
             20                  25                  30

Asn
```

<210> SEQ ID NO 13
<211> LENGTH: 33
<212> TYPE: PRT
<213> ORGANISM: Human immunodeficiency virus type 1

<400> SEQUENCE: 13

```
Arg Leu Gln Ala Leu Glu Thr Leu Ile Gln Asn Gln Gln Arg Leu Asp
  1               5                  10                  15

Leu Trp Gly Cys Lys Gly Arg Ile Ile Cys Tyr Thr Ser Val Lys Trp
             20                  25                  30

Asn
```

<210> SEQ ID NO 14
<211> LENGTH: 33
<212> TYPE: PRT
<213> ORGANISM: Human immunodeficiency virus type 1

<400> SEQUENCE: 14

```
Arg Leu Leu Ala Leu Glu Thr Phe Ile Gln Asn Gln Gln Leu Leu Asn
  1               5                  10                  15

Leu Trp Gly Cys Lys Gly Arg Leu Ile Cys Tyr Thr Ser Val Lys Trp
             20                  25                  30

Asn
```

-continued

<210> SEQ ID NO 15
<211> LENGTH: 33
<212> TYPE: PRT
<213> ORGANISM: Human immunodeficiency virus type 1

<400> SEQUENCE: 15

Arg Leu Leu Ala Leu Glu Thr Leu Ile Gln Asn Gln Gln Leu Leu Asn
1 5 10 15

Leu Trp Gly Cys Lys Gly Arg Leu Val Cys Tyr Thr Ser Val Lys Trp
20 25 30

Asn

<210> SEQ ID NO 16
<211> LENGTH: 33
<212> TYPE: PRT
<213> ORGANISM: Human immunodeficiency virus type 1

<400> SEQUENCE: 16

Arg Leu Leu Ala Leu Glu Thr Leu Ile Gln Asn Gln Gln Leu Leu Asn
1 5 10 15

Ser Trp Gly Cys Gln Gly Lys Leu Val Cys Tyr Thr Ser Val Ile Trp
20 25 30

Asn

<210> SEQ ID NO 17
<211> LENGTH: 33
<212> TYPE: PRT
<213> ORGANISM: Human immunodeficiency virus type 1

<400> SEQUENCE: 17

Arg Leu Gln Ala Leu Glu Thr Leu Met Gln Asn Gln Gln Leu Leu Asn
1 5 10 15

Leu Trp Gly Cys Lys Gly Lys Ser Ile Cys Tyr Thr Ser Val Lys Trp
20 25 30

Asn

<210> SEQ ID NO 18
<211> LENGTH: 33
<212> TYPE: PRT
<213> ORGANISM: Human immunodeficiency virus type 1

<400> SEQUENCE: 18

Arg Leu Leu Ala Leu Glu Thr Phe Val Gln Asn Gln Gln Leu Leu Asn
1 5 10 15

Leu Trp Gly Cys Lys Gly Arg Ile Val Cys Tyr Thr Ser Val Lys Trp
20 25 30

Asn

<210> SEQ ID NO 19
<211> LENGTH: 33
<212> TYPE: PRT
<213> ORGANISM: Human immunodeficiency virus type 1

<400> SEQUENCE: 19

Arg Leu Leu Ala Leu Glu Thr Leu Met Gln Asn Gln Gln Leu Leu Asn
1 5 10 15

Leu Trp Gly Cys Arg Gly Lys Ala Ile Cys Tyr Thr Ser Val Gln Trp
20 25 30

Asn

-continued

<210> SEQ ID NO 20
<211> LENGTH: 33
<212> TYPE: PRT
<213> ORGANISM: Human immunodeficiency virus type 1

<400> SEQUENCE: 20

Arg Leu Gln Ala Leu Glu Thr Leu Ile Gln Asn Gln Gln Leu Leu Ser
1 5 10 15

Leu Trp Gly Cys Lys Gly Arg Leu Val Cys Tyr Thr Ser Val Lys Trp
20 25 30

His

<210> SEQ ID NO 21
<211> LENGTH: 33
<212> TYPE: PRT
<213> ORGANISM: Human immunodeficiency virus type 1

<400> SEQUENCE: 21

Arg Leu Leu Ala Leu Glu Thr Leu Ile Gln Asn Gln Gln Leu Leu Asn
1 5 10 15

Leu Trp Gly Cys Lys Gly Arg Leu Leu Cys Tyr Thr Ser Val Lys Trp
20 25 30

Asn

<210> SEQ ID NO 22
<211> LENGTH: 33
<212> TYPE: PRT
<213> ORGANISM: Human immunodeficiency virus type 1

<400> SEQUENCE: 22

Arg Leu Leu Ala Leu Glu Thr Phe Ile Gln Asn Gln Gln Leu Leu Asn
1 5 10 15

Leu Trp Gly Cys Lys Gly Lys Leu Ile Cys Tyr Thr Ser Val Glu Trp
20 25 30

Asn

<210> SEQ ID NO 23
<211> LENGTH: 33
<212> TYPE: PRT
<213> ORGANISM: Human immunodeficiency virus type 1

<400> SEQUENCE: 23

Arg Leu Gln Ala Leu Glu Thr Leu Met Gln Asn Gln Gln Arg Leu Asp
1 5 10 15

Leu Trp Gly Cys Lys Gly Arg Leu Ile Cys Tyr Thr Ser Val Lys Trp
20 25 30

Asn

<210> SEQ ID NO 24
<211> LENGTH: 33
<212> TYPE: PRT
<213> ORGANISM: Human immunodeficiency virus type 1

<400> SEQUENCE: 24

Arg Leu Gln Ala Leu Glu Pro Leu Ile Gln Asn Gln Gln Arg Leu Ser
1 5 10 15

Leu Trp Gly Cys Lys Gly Arg Ile Ile Cys Tyr Thr Ser Ala Lys Trp
20 25 30

-continued

Asn

<210> SEQ ID NO 25
<211> LENGTH: 33
<212> TYPE: PRT
<213> ORGANISM: Human immunodeficiency virus type 1

<400> SEQUENCE: 25

Arg Leu Leu Ala Leu Glu Thr Leu Ile Gln Asn Gln Gln Leu Leu Asn
1 5 10 15

Ser Trp Gly Cys Lys Gly Arg Leu Val Cys Tyr Thr Ser Val Lys Trp
20 25 30

Asn

<210> SEQ ID NO 26
<211> LENGTH: 33
<212> TYPE: PRT
<213> ORGANISM: Human immunodeficiency virus type 1

<400> SEQUENCE: 26

Arg Leu Val Ala Leu Glu Thr Leu Val Gln Asn Gln Gln Leu Leu Asn
1 5 10 15

Leu Trp Gly Cys Lys Gly Arg Leu Thr Cys Tyr Thr Ser Val Lys Trp
20 25 30

Asn

<210> SEQ ID NO 27
<211> LENGTH: 33
<212> TYPE: PRT
<213> ORGANISM: Human immunodeficiency virus type 1

<400> SEQUENCE: 27

Arg Leu Leu Ala Leu Glu Thr Leu Ile Gln Asn Gln Gln Leu Leu Asn
1 5 10 15

Leu Trp Gly Cys Lys Gly Arg Leu Leu Cys Tyr Thr Ser Val Lys Trp
20 25 30

Asn

<210> SEQ ID NO 28
<211> LENGTH: 33
<212> TYPE: PRT
<213> ORGANISM: Human immunodeficiency virus type 1

<400> SEQUENCE: 28

Arg Leu Leu Ala Leu Glu Thr Phe Ile Gln Asn Gln Gln Leu Leu Asn
1 5 10 15

Leu Trp Gly Cys Lys Gly Gln Leu Val Cys Tyr Thr Ser Val Lys Trp
20 25 30

Asn

<210> SEQ ID NO 29
<211> LENGTH: 33
<212> TYPE: PRT
<213> ORGANISM: Human immunodeficiency virus type 1

<400> SEQUENCE: 29

Arg Leu Leu Ala Leu Glu Thr Phe Ile Gln Asn Gln Gln Leu Leu Asn
1 5 10 15

Leu Trp Gly Cys Lys Gly Arg Leu Ile Cys Tyr Thr Ser Val Lys Trp
20 25 30

-continued

```
Asn


<210> SEQ ID NO 30
<211> LENGTH: 33
<212> TYPE: PRT
<213> ORGANISM: Human immunodeficiency virus type 1

<400> SEQUENCE: 30

Arg Leu Leu Ala Leu Glu Thr Leu Ile Gln Asn Gln Gln Leu Leu Asn
  1               5                  10                  15

Ser Trp Gly Cys Lys Gly Arg Ile Val Cys Tyr Thr Ser Val Lys Trp
             20                  25                  30

Asn


<210> SEQ ID NO 31
<211> LENGTH: 33
<212> TYPE: PRT
<213> ORGANISM: Human immunodeficiency virus type 1

<400> SEQUENCE: 31

Glu Arg Glu Ile Asp Asn Tyr Thr Ser Leu Ile Tyr Ser Leu Leu Glu
  1               5                  10                  15

Lys Ser Gln Thr Gln Gln Glu Lys Asn Glu Gln Glu Leu Leu Glu Leu
             20                  25                  30

Asp


<210> SEQ ID NO 32
<211> LENGTH: 33
<212> TYPE: PRT
<213> ORGANISM: Human immunodeficiency virus type 1

<400> SEQUENCE: 32

Asp Arg Gln Ile Ser Asn Ile Ser Ser Thr Ile Tyr Glu Glu Ile Gln
  1               5                  10                  15

Lys Ala Gln Val Gln Gln Glu Gln Asn Glu Lys Lys Leu Leu Glu Leu
             20                  25                  30

Asp


<210> SEQ ID NO 33
<211> LENGTH: 33
<212> TYPE: PRT
<213> ORGANISM: Human immunodeficiency virus type 1

<400> SEQUENCE: 33

Asp Gln His Ile Asn Asn Val Ser Ser Ile Ile Tyr Asp Glu Ile Gln
  1               5                  10                  15

Ala Ala Gln Asp Gln Gln Glu Lys Asn Val Lys Ala Leu Leu Glu Leu
             20                  25                  30

Asp


<210> SEQ ID NO 34
<211> LENGTH: 33
<212> TYPE: PRT
<213> ORGANISM: Human immunodeficiency virus type 1

<400> SEQUENCE: 34

Asp Gln Gln Ile Asn Asn Val Ser Ser Phe Ile Tyr Glu Lys Ile Gln
  1               5                  10                  15

Glu Ala Gln Glu Gln Gln Glu Lys Asn Glu Lys Glu Leu Leu Glu Leu
```

-continued 20 25 30

Asp

<210> SEQ ID NO 35
<211> LENGTH: 33
<212> TYPE: PRT
<213> ORGANISM: Human immunodeficiency virus type 1

<400> SEQUENCE: 35

Asp Gln Gln Ile Asp Asn Ile Ser Ser Thr Ile Tyr Asp Glu Ile Gln
1 5 10 15

Lys Ala Gln Val Gln Gln Glu Gln Asn Glu Gln Lys Leu Leu Glu Leu
20 25 30

Asp

<210> SEQ ID NO 36
<211> LENGTH: 33
<212> TYPE: PRT
<213> ORGANISM: Human immunodeficiency virus type 1

<400> SEQUENCE: 36

Asp Gln Gln Ile Asn Asn Ile Ser Ser Ile Ile Tyr Gly Glu Ile Gln
1 5 10 15

Lys Ala Gln Val Gln Gln Glu Glu Asn Glu Lys Lys Leu Leu Glu Leu
20 25 30

Asp

<210> SEQ ID NO 37
<211> LENGTH: 33
<212> TYPE: PRT
<213> ORGANISM: Human immunodeficiency virus type 1

<400> SEQUENCE: 37

Asp Gln Gln Ile Asn Asn Ile Ser Ser Ile Ile Tyr Gly Glu Ile Gln
1 5 10 15

Lys Ala Gln Val Gln Gln Glu His Asn Glu Lys Lys Leu Leu Glu Leu
20 25 30

Asp

<210> SEQ ID NO 38
<211> LENGTH: 33
<212> TYPE: PRT
<213> ORGANISM: Human immunodeficiency virus type 1

<400> SEQUENCE: 38

Asp Gln Gln Val Asn Asn Val Ser Ser Phe Ile Tyr Asp Lys Ile Gln
1 5 10 15

Glu Ala Gln Glu Gln Gln Glu Glu Asn Glu Arg Ala Leu Leu Glu Leu
20 25 30

Asp

<210> SEQ ID NO 39
<211> LENGTH: 33
<212> TYPE: PRT
<213> ORGANISM: Human immunodeficiency virus type 1

<400> SEQUENCE: 39

Asp Gln Gln Ile Ser Asn Val Ser Ser Ile Ile Tyr Glu Glu Ile Gln
1 5 10 15

-continued

Lys Ala Gln Glu Gln Gln Glu Gln Asn Glu Lys Lys Leu Leu Glu Leu
20 25 30

Asp

<210> SEQ ID NO 40
<211> LENGTH: 33
<212> TYPE: PRT
<213> ORGANISM: Human immunodeficiency virus type 1

<400> SEQUENCE: 40

Asp Gln Gln Ile Ala Asn Val Ser Ser Phe Ile Tyr Asp Gln Ile Gln
1 5 10 15

Glu Ala Gln Glu Arg Gln Asp Lys Asn Glu Lys Thr Leu Leu Glu Leu
20 25 30

Asp

<210> SEQ ID NO 41
<211> LENGTH: 33
<212> TYPE: PRT
<213> ORGANISM: Human immunodeficiency virus type 1

<400> SEQUENCE: 41

Asp Gln Gln Ile Asp Asn Val Ser Ser Thr Ile Tyr Glu Glu Ile Leu
1 5 10 15

Lys Ala Gln Ile Gln Gln Glu Gln Asn Glu Lys Lys Leu Leu Glu Leu
20 25 30

Asp

<210> SEQ ID NO 42
<211> LENGTH: 33
<212> TYPE: PRT
<213> ORGANISM: Human immunodeficiency virus type 1

<400> SEQUENCE: 42

Asp Arg Glu Ile Asp Asn Ile Ser Ser Tyr Ile Tyr Glu Lys Ile Gln
1 5 10 15

Glu Ala Gln Asp Gln Gln Glu Asn Asn Glu Arg Glu Leu Leu Glu Leu
20 25 30

Asp

<210> SEQ ID NO 43
<211> LENGTH: 33
<212> TYPE: PRT
<213> ORGANISM: Human immunodeficiency virus type 1

<400> SEQUENCE: 43

Asp Lys Gln Ile Ser Asn Ile Ser Ser Ile Ile Tyr Asp Glu Ile Gln
1 5 10 15

Thr Ala Gln Asp Gln Gln Glu Arg Asn Val Lys Ala Leu Leu Glu Leu
20 25 30

Asp

<210> SEQ ID NO 44
<211> LENGTH: 33
<212> TYPE: PRT
<213> ORGANISM: Human immunodeficiency virus type 1

<400> SEQUENCE: 44

Asp Gln Gln Val Asn Asn Val Ser Ser Ile Ile Tyr Glu Glu Ile Gln
1 5 10 15

-continued

```
Arg Ala Gln Val Gln Gln Glu Gln Asn Glu Lys Arg Leu Leu Glu Leu
            20                  25                  30

Asp


<210> SEQ ID NO 45
<211> LENGTH: 33
<212> TYPE: PRT
<213> ORGANISM: Human immunodeficiency virus type 1

<400> SEQUENCE: 45

Asp Gln Gln Ile Asp Asn Val Ser Ser Ile Ile Tyr Glu Glu Ile Gln
  1               5                  10                  15

Lys Ala Gln Gly Gln Gln Glu Gln Asn Glu Lys Lys Leu Leu Glu Leu
            20                  25                  30

Asp


<210> SEQ ID NO 46
<211> LENGTH: 63
<212> TYPE: DNA
<213> ORGANISM: Artificial Sequence
<220> FEATURE:
<223> OTHER INFORMATION: Description of Artificial Sequence:  HIV
      Consensus Sequence

<400> SEQUENCE: 46

attttggaag cccaggatca acaagaggag aacgttcgtg agttgctgga gctagataaa     60

tgg                                                                   63


<210> SEQ ID NO 47
<211> LENGTH: 58
<212> TYPE: DNA
<213> ORGANISM: Artificial Sequence
<220> FEATURE:
<223> OTHER INFORMATION: Description of Artificial Sequence:  HIV
      Consensus Sequence

<400> SEQUENCE: 47

agcaagttaa caatgtttct tctattattt atgataagat tttggaagcc caggatca       58


<210> SEQ ID NO 48
<211> LENGTH: 63
<212> TYPE: DNA
<213> ORGANISM: Artificial Sequence
<220> FEATURE:
<223> OTHER INFORMATION: Description of Artificial Sequence:  HIV
      Consensus Sequence

<400> SEQUENCE: 48

attttggaag cccaggatca acaagaggag aacgttcgtg agttgctgga gctagataaa     60

tgg                                                                   63


<210> SEQ ID NO 49
<211> LENGTH: 58
<212> TYPE: DNA
<213> ORGANISM: Artificial Sequence
<220> FEATURE:
<223> OTHER INFORMATION: Description of Artificial Sequence:  HIV
      Consensus Sequence

<400> SEQUENCE: 49

agcaagttaa caatgtttct tctattattt atgataagat tttggaagcc caggatca       58
```

-continued

<210> SEQ ID NO 50
<211> LENGTH: 62
<212> TYPE: DNA
<213> ORGANISM: Artificial Sequence
<220> FEATURE:
<223> OTHER INFORMATION: Description of Artificial Sequence: HIV
Consensus Sequence

<400> SEQUENCE: 50
ccagatatcc tccagagact tattagacca agaagcatgc caacgggcac tagtataaca 60
aa 62

<210> SEQ ID NO 51
<211> LENGTH: 62
<212> TYPE: DNA
<213> ORGANISM: Artificial Sequence
<220> FEATURE:
<223> OTHER INFORMATION: Description of Artificial Sequence: HIV
Consensus Sequence

<400> SEQUENCE: 51
acattgttaa cttgctggtc ccattgcatc caggtcatgt tatcccagat atcctccaga 60
ga 62

<210> SEQ ID NO 52
<211> LENGTH: 62
<212> TYPE: DNA
<213> ORGANISM: Artificial Sequence
<220> FEATURE:
<223> OTHER INFORMATION: Description of Artificial Sequence: HIV
Consensus Sequence

<400> SEQUENCE: 52
ccagatatcc tccagagact tattagacca agaagcatgc caacgggcac tagtataaca 60
aa 62

<210> SEQ ID NO 53
<211> LENGTH: 62
<212> TYPE: DNA
<213> ORGANISM: Artificial Sequence
<220> FEATURE:
<223> OTHER INFORMATION: Description of Artificial Sequence: HIV
Consensus Sequence

<400> SEQUENCE: 53
acattgttaa cttgctggtc ccattgcatc caggtcatgt tatcccagat atcctccaga 60
ga 62

<210> SEQ ID NO 54
<211> LENGTH: 25
<212> TYPE: DNA
<213> ORGANISM: Artificial Sequence
<220> FEATURE:
<223> OTHER INFORMATION: Description of Artificial Sequence: HIV
Consensus Sequence

<400> SEQUENCE: 54
accggaattc cgatttcctt gggtt 25

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: HIV -continued Consensus Sequence

<400> SEQUENCE: 55
cataaagctt gtcccagaag ttcc 24

<210> SEQ ID NO 56
<211> LENGTH: 26
<212> TYPE: DNA
<213> ORGANISM: Artificial Sequence
<220> FEATURE:
<223> OTHER INFORMATION: Description of Artificial Sequence: HIV
Consensus Sequence

<400> SEQUENCE: 56
gccactgcag ccagactatt attgtc 26

<210> SEQ ID NO 57
<211> LENGTH: 439
<212> TYPE: PRT
<213> ORGANISM: Artificial Sequence
<220> FEATURE:
<223> OTHER INFORMATION: Description of Artificial Sequence: HIV
Consensus Sequence

<400> SEQUENCE: 57

```
Met Arg Gly Ser Gly Ile Met Val Arg Pro Leu Asn Ser Ile Val Ala
  1               5                  10                  15

Val Ser Gln Asn Met Gly Ile Gly Lys Asn Gly Asp Leu Pro Trp Pro
             20                  25                  30

Pro Leu Arg Asn Glu Phe Lys Tyr Phe Gln Arg Met Thr Thr Thr Ser
         35                  40                  45

Ser Val Glu Gly Lys Gln Asn Leu Val Ile Met Gly Arg Lys Thr Trp
     50                  55                  60

Phe Ser Ile Pro Glu Lys Asn Arg Pro Leu Lys Asp Arg Ile Asn Ile
 65                  70                  75                  80

Val Leu Ser Arg Glu Leu Lys Glu Pro Pro Arg Gly Ala His Phe Leu
                 85                  90                  95

Ala Lys Ser Leu Asp Asp Ala Leu Arg Leu Ile Glu Gln Pro Glu Leu
            100                 105                 110

Ala Ser Lys Val Asp Met Val Trp Ile Val Gly Gly Ser Ser Val Tyr
        115                 120                 125

Gln Glu Ala Met Asn Gln Pro Gly His Leu Arg Leu Phe Val Thr Arg
    130                 135                 140

Ile Met Gln Glu Phe Glu Ser Asp Thr Phe Phe Pro Glu Ile Asp Leu
145                 150                 155                 160

Gly Lys Tyr Lys Leu Leu Pro Glu Tyr Pro Gly Val Leu Ser Glu Val
                165                 170                 175

Gln Glu Glu Lys Gly Ile Lys Tyr Lys Phe Glu Val Tyr Glu Lys Lys
            180                 185                 190

Gly Ser Arg Ser Ala Arg Leu Leu Leu Ser Gly Ile Val Gln Gln Gln
        195                 200                 205

Asn Asn Leu Leu Arg Ala Ile Glu Ala Gln Gln His Met Leu Gln Leu
    210                 215                 220

Thr Ala Trp Gly Ile Lys Gln Leu Arg Ala Arg Leu Gln Ala Leu Glu
225                 230                 235                 240

Thr Leu Met Gln Asn Gln Gln Arg Leu Asn Ser Trp Gly Cys Lys Gly
                245                 250                 255

Arg Ile Ile Cys Tyr Thr Ser Ala Arg Trp His Ala Ser Trp Ser Asn
```

-continued

```
            260                 265                 270

Lys Ser Leu Glu Asp Ile Trp Asp Asn Met Thr Trp Met Gln Trp Asp
        275                 280                 285

Gln Gln Val Asn Asn Val Ser Ser Ile Ile Tyr Asp Lys Ile Leu Glu
    290                 295                 300

Ala Gln Asp Gln Gln Glu Glu Asn Val Arg Glu Leu Leu Glu Leu Asp
305                 310                 315                 320

Lys Trp Ala Ser Leu Trp Asn Trp Phe Asp Ile Thr Asn Trp Leu Trp
                325                 330                 335

Tyr Ile Lys Ile Phe Ile Met Ile Val Gly Gly Leu Val Gly Leu Arg
            340                 345                 350

Ile Val Phe Ala Val Leu Ser Ile Val Asn Arg Val Arg Gln Gly Tyr
        355                 360                 365

Ser Pro Leu Ser Leu Gln Thr Arg Pro Pro Val Pro Arg Gly Pro Asp
    370                 375                 380

Arg Pro Glu Gly Ile Glu Glu Glu Gly Gly Glu Arg Asp Arg Asp Thr
385                 390                 395                 400

Ser Gly Arg Leu Val His Gly Phe Leu Ala Ile Ile Trp Val Asp Leu
                405                 410                 415

Gly Pro Glu Gln Lys Leu Ile Ser Glu Glu Asp Leu Asn Ser Ala Val
            420                 425                 430

Asp His His His His His His
        435


<210> SEQ ID NO 58
<211> LENGTH: 368
<212> TYPE: PRT
<213> ORGANISM: Artificial Sequence
<220> FEATURE:
<223> OTHER INFORMATION: Description of Artificial Sequence:  HIV
      Consensus Sequence

<400> SEQUENCE: 58

Met Arg Gly Ser Gly Ile Met Val Arg Pro Leu Asn Ser Ile Val Ala
  1               5                  10                  15

Val Ser Gln Asn Met Gly Ile Gly Lys Asn Gly Asp Leu Pro Trp Pro
            20                  25                  30

Pro Leu Arg Asn Glu Phe Lys Tyr Phe Gln Arg Met Thr Thr Thr Ser
        35                  40                  45

Ser Val Glu Gly Lys Gln Asn Leu Val Ile Met Gly Arg Lys Thr Trp
     50                  55                  60

Phe Ser Ile Pro Glu Lys Asn Arg Pro Leu Lys Asp Arg Ile Asn Ile
 65                  70                  75                  80

Val Leu Ser Arg Glu Leu Lys Glu Pro Pro Arg Gly Ala His Phe Leu
                85                  90                  95

Ala Lys Ser Leu Asp Asp Ala Leu Arg Leu Ile Glu Gln Pro Glu Leu
            100                 105                 110

Ala Ser Lys Val Asp Met Val Trp Ile Val Gly Gly Ser Ser Val Tyr
        115                 120                 125

Gln Glu Ala Met Asn Gln Pro Gly His Leu Arg Leu Phe Val Thr Arg
    130                 135                 140

Ile Met Gln Glu Phe Glu Ser Asp Thr Phe Phe Pro Glu Ile Asp Leu
145                 150                 155                 160

Gly Lys Tyr Lys Leu Leu Pro Glu Tyr Pro Gly Val Leu Ser Glu Val
                165                 170                 175
```

-continued

```
Gln Glu Glu Lys Gly Ile Lys Tyr Lys Phe Glu Val Tyr Glu Lys Lys
            180                 185                 190

Gly Ser Arg Ser Ala Arg Leu Leu Leu Ser Gly Ile Val Gln Gln Gln
        195                 200                 205

Asn Asn Leu Leu Arg Ala Ile Glu Ala Gln Gln His Met Leu Gln Leu
    210                 215                 220

Thr Ala Trp Gly Ile Lys Gln Leu Arg Ala Arg Leu Gln Ala Leu Glu
225                 230                 235                 240

Thr Leu Met Gln Asn Gln Gln Arg Leu Asn Ser Trp Gly Cys Lys Gly
                245                 250                 255

Arg Ile Ile Cys Tyr Thr Ser Ala Arg Trp His Ala Ser Trp Ser Asn
            260                 265                 270

Lys Ser Leu Glu Asp Ile Trp Asp Asn Met Thr Trp Met Gln Trp Asp
        275                 280                 285

Gln Gln Val Asn Asn Val Ser Ser Ile Ile Tyr Asp Lys Ile Leu Glu
    290                 295                 300

Ala Gln Asp Gln Gln Glu Glu Asn Val Arg Glu Leu Leu Glu Leu Asp
305                 310                 315                 320

Lys Trp Ala Ser Leu Trp Asn Trp Phe Asp Ile Thr Asn Trp Leu Trp
                325                 330                 335

Tyr Ile Lys Ile Phe Ile Met Ile Val Gly Pro Glu Gln Lys Leu Ile
            340                 345                 350

Ser Glu Glu Asp Leu Asn Ser Ala Val Asp His His His His His His
        355                 360                 365
```

<210> SEQ ID NO 59
<211> LENGTH: 23
<212> TYPE: PRT
<213> ORGANISM: Artificial Sequence
<220> FEATURE:
<223> OTHER INFORMATION: Description of Artificial Sequence: HIV Consensus Sequence

<400> SEQUENCE: 59

```
Asn Gln Gln Arg Leu Asn Ser Trp Gly Cys Lys Gly Arg Ile Ile Cys
  1               5                  10                  15

Tyr Thr Ser Ala Arg Trp His
             20
```

<210> SEQ ID NO 60
<211> LENGTH: 23
<212> TYPE: PRT
<213> ORGANISM: Artificial Sequence
<220> FEATURE:
<221> NAME/KEY: Xaa is any amino acid
<222> LOCATION: 1
<223> OTHER INFORMATION: Description of Artificial Sequence: HIV Consensus Sequence

<400> SEQUENCE: 60

```
Xaa Gln Gln Arg Leu Asn Ser Trp Gly Cys Lys Gly Arg Ile Ile Cys
  1               5                  10                  15

Tyr Thr Ser Ala Arg Trp His
             20
```

<210> SEQ ID NO 61
<211> LENGTH: 23
<212> TYPE: PRT
<213> ORGANISM: Artificial Sequence
<220> FEATURE:
<223> OTHER INFORMATION: Description of Artificial Sequence: HIV -continued

```
      Consensus Sequence

<400> SEQUENCE: 61

Glu Gln Gln Arg Leu Asn Ser Trp Gly Cys Lys Gly Arg Ile Ile Cys
  1               5                  10                  15

Tyr Thr Ser Ala Arg Trp His
             20


<210> SEQ ID NO 62
<211> LENGTH: 28
<212> TYPE: PRT
<213> ORGANISM: Artificial Sequence
<220> FEATURE:
<221> NAME/KEY: Xaa is any amino acid
<222> LOCATION: 6
<223> OTHER INFORMATION: Description of Artificial Sequence:  HIV
      Consensus Sequence

<400> SEQUENCE: 62

Glu Thr Leu Met Gln Xaa Gln Gln Arg Leu Asn Ser Trp Gly Cys Lys
  1               5                  10                  15

Gly Arg Ile Ile Cys Tyr Thr Ser Ala Arg Trp His
             20                  25


<210> SEQ ID NO 63
<211> LENGTH: 30
<212> TYPE: PRT
<213> ORGANISM: Artificial Sequence
<220> FEATURE:
<221> NAME/KEY: Xaa is any amino acid
<222> LOCATION: 8
<223> OTHER INFORMATION: Description of Artificial Sequence:  HIV
      Consensus Sequence

<400> SEQUENCE: 63

Gly Arg Glu Thr Leu Met Gln Xaa Gln Gln Arg Leu Asn Ser Trp Gly
  1               5                  10                  15

Cys Lys Gly Arg Ile Ile Cys Tyr Thr Ser Ala Arg Trp His
             20                  25                  30


<210> SEQ ID NO 64
<211> LENGTH: 35
<212> TYPE: PRT
<213> ORGANISM: Artificial Sequence
<220> FEATURE:
<221> NAME/KEY: Xaa is any amino acid
<222> LOCATION: 13
<223> OTHER INFORMATION: Description of Artificial Sequence:  HIV
      Consensus Sequence

<400> SEQUENCE: 64

Arg Ala Arg Leu Gln Ala Leu Glu Thr Leu Met Gln Xaa Gln Gln Arg
  1               5                  10                  15

Leu Asn Ser Trp Gly Cys Lys Gly Arg Ile Ile Cys Tyr Thr Ser Ala
             20                  25                  30

Arg Trp His
         35


<210> SEQ ID NO 65
<211> LENGTH: 33
<212> TYPE: PRT
<213> ORGANISM: Artificial Sequence
<220> FEATURE:
<223> OTHER INFORMATION: Description of Artificial Sequence:  HIV
      Consensus Sequence
```

-continued

<400> SEQUENCE: 65

Asp Gln Gln Val Asn Asn Val Ser Ser Ile Ile Tyr Asp Lys Ile Leu
1 5 10 15

Glu Ala Gln Asp Gln Gln Glu Glu Asn Val Arg Glu Leu Leu Glu Leu
20 25 30

Asp

<210> SEQ ID NO 66
<211> LENGTH: 220
<212> TYPE: PRT
<213> ORGANISM: Artificial Sequence
<220> FEATURE:
<223> OTHER INFORMATION: Description of Artificial Sequence: HIV
Consensus Sequence

<400> SEQUENCE: 66

Ala Arg Leu Leu Leu Ser Gly Ile Val Gln Gln Gln Asn Asn Leu Leu
1 5 10 15

Arg Ala Ile Glu Ala Gln Gln His Met Leu Gln Leu Thr Ala Trp Gly
20 25 30

Ile Lys Gln Leu Arg Ala Arg Leu Gln Ala Leu Glu Thr Leu Met Gln
35 40 45

Asn Gln Gln Arg Leu Asn Ser Trp Gly Cys Lys Gly Arg Ile Ile Cys
50 55 60

Tyr Thr Ser Ala Arg Trp His Ala Ser Trp Ser Asn Lys Ser Leu Glu
65 70 75 80

Asp Ile Trp Asp Asn Met Thr Trp Met Gln Trp Asp Gln Gln Val Asn
85 90 95

Asn Val Ser Ser Ile Ile Tyr Asp Lys Ile Leu Glu Ala Gln Asp Gln
100 105 110

Gln Glu Glu Asn Val Arg Glu Leu Leu Glu Leu Asp Lys Trp Ala Ser
115 120 125

Leu Trp Asn Trp Phe Asp Ile Thr Asn Trp Leu Trp Tyr Ile Lys Ile
130 135 140

Phe Ile Met Ile Val Gly Gly Leu Val Gly Leu Arg Ile Val Phe Ala
145 150 155 160

Val Leu Ser Ile Val Asn Arg Val Arg Gln Gly Tyr Ser Pro Leu Ser
165 170 175

Leu Gln Thr Arg Pro Pro Val Pro Arg Gly Pro Asp Arg Pro Glu Gly
180 185 190

Ile Glu Glu Glu Gly Gly Glu Arg Asp Arg Asp Thr Ser Gly Arg Leu
195 200 205

Val His Gly Phe Leu Ala Ile Ile Trp Val Asp Leu
210 215 220

<210> SEQ ID NO 67
<211> LENGTH: 149
<212> TYPE: PRT
<213> ORGANISM: Artificial Sequence
<220> FEATURE:
<223> OTHER INFORMATION: Description of Artificial Sequence: HIV
Consensus Sequence

<400> SEQUENCE: 67

Ala Arg Leu Leu Leu Ser Gly Ile Val Gln Gln Gln Asn Asn Leu Leu
1 5 10 15

Arg Ala Ile Glu Ala Gln Gln His Met Leu Gln Leu Thr Ala Trp Gly
20 25 30

-continued

```
Ile Lys Gln Leu Arg Ala Arg Leu Gln Ala Leu Glu Thr Leu Met Gln
         35                  40                  45

Asn Gln Gln Arg Leu Asn Ser Trp Gly Cys Lys Gly Arg Ile Ile Cys
     50                  55                  60

Tyr Thr Ser Ala Arg Trp His Ala Ser Trp Ser Asn Lys Ser Leu Glu
 65                  70                  75                  80

Asp Ile Trp Asp Asn Met Thr Trp Met Gln Trp Asp Gln Gln Val Asn
                 85                  90                  95

Asn Val Ser Ser Ile Ile Tyr Asp Lys Ile Leu Glu Ala Gln Asp Gln
            100                 105                 110

Gln Glu Glu Asn Val Arg Glu Leu Leu Glu Leu Asp Lys Trp Ala Ser
        115                 120                 125

Leu Trp Asn Trp Phe Asp Ile Thr Asn Trp Leu Trp Tyr Ile Lys Ile
    130                 135                 140

Phe Ile Met Ile Val
145


<210> SEQ ID NO 68
<211> LENGTH: 23
<212> TYPE: PRT
<213> ORGANISM: Human immunodeficiency virus type 1

<400> SEQUENCE: 68

Asn Gln Gln Leu Leu Ser Leu Trp Gly Cys Lys Gly Lys Leu Val Cys
  1               5                  10                  15

Tyr Thr Ser Val Lys Trp Asn
             20


<210> SEQ ID NO 69
<211> LENGTH: 30
<212> TYPE: PRT
<213> ORGANISM: Artificial Sequence
<220> FEATURE:
<223> OTHER INFORMATION: Description of Artificial Sequence:  HIV
      Consensus Sequence

<400> SEQUENCE: 69

Gly Arg Glu Thr Leu Met Gln Asp Gln Gln Arg Leu Asn Ser Trp Gly
  1               5                  10                  15

Cys Lys Gly Arg Ile Ile Cys Tyr Thr Ser Ala Arg Trp His
             20                  25                  30


<210> SEQ ID NO 70
<211> LENGTH: 160
<212> TYPE: PRT
<213> ORGANISM: Human immunodeficiency virus type 1

<400> SEQUENCE: 70

Ala Ala Ile Gly Ala Leu Phe Leu Gly Phe Leu Gly Ala Ala Gly Ser
  1               5                  10                  15

Thr Met Gly Ala Ala Ser Val Thr Leu Thr Val Gln Ala Arg Leu Leu
             20                  25                  30

Leu Ser Gly Ile Val Gln Gln Gln Asn Asn Leu Leu Arg Ala Ile Glu
         35                  40                  45

Ala Gln Gln His Met Leu Gln Leu Thr Val Trp Gly Ile Lys Gln Leu
     50                  55                  60

Gln Ala Arg Val Leu Ala Val Glu Arg Tyr Leu Lys Asp Gln Gln Leu
 65                  70                  75                  80
```

-continued

```
Leu Gly Phe Trp Gly Cys Ser Gly Lys Leu Ile Cys Thr Thr Thr Val
                 85                  90                  95

Pro Trp Asn Ala Ser Trp Ser Asn Lys Ser Leu Asp Asp Ile Trp Asn
            100                 105                 110

Asn Met Thr Trp Met Gln Trp Glu Arg Glu Ile Asp Asn Tyr Thr Ser
        115                 120                 125

Leu Ile Tyr Ser Leu Leu Glu Lys Ser Gln Thr Gln Gln Glu Lys Asn
    130                 135                 140

Glu Gln Glu Leu Leu Glu Leu Asp Lys Trp Ala Ser Leu Trp Asn Trp
145                 150                 155                 160
```

PEPTIDES FOR THE DETECTION OF HIV-1 GROUP O

BACKGROUND

The principal etiological agent responsible for causing what has come to be known as acquired immunodeficiency syndrome (AIDS) is a non-transforming retrovirus belonging to the lentivirus genus (1). This virus, referred to as Human Immunodeficiency Virus type I (HIV-1), is now widely disseminated and constitutes a serious threat to health and productivity worldwide. Virtually all industrialized countries, as well as many in the developing world, now mandate the testing of blood donations to prevent the further transmission of this virus and the spread of disease through the use of contaminated blood and blood products. A related, genetically distinct, but less wide-spread and pathologically less aggressive virus capable of inducing similar disease was reported in 1986, and is referred to as HIV-2 (2). While HIV-2 is found primarily in West Africa and is less widely disseminated than HIV-1, many countries require the screening of blood donations for antibodies to this virus as well. An HIV-1 is disclosed in EP-178 978, while an HIV-2 is disclosed in EP-0 239 425.

One feature which is characteristic of human immunodeficiency viruses is their sequence variability. The genomes of all HIVs encode the enzyme reverse transcriptase. This enzyme, which the virus requires to convert its RNA genome into its double-stranded DNA equivalent prior to integration into host cell DNA, is essential for virus replication. Unlike many polymerases, this $Mg^{+2}$-dependent enzyme lacks a 3'→5' exonuclease activity which normally serves a proofreading function. As a consequence, this enzyme tends to be error-prone. Within any HIV-infected individual, many naturally occurring sequence variants of the virus can be found, not all of which are viable. This observation has given rise to the notion of the quasi-species, a term used to describe a particular strain of HIV infecting an individual as a collection of all its closely related, naturally occurring sequence variants (3).

In addition to naturally occurring sequence variants within an infected individual, phylogenetic analyses of HIV-1 strains collected from all over the world have demonstrated that these strains can be grouped into at least 9 types (A–I) based on the similarity of their sequences (4). The differences between the types are greater than the differences observed between individual virus variants within a single infected person, or the differences between other variants belonging to the same type. The geographical distribution of these HIV-1 types varies significantly, with certain types being prevalent in one particular geographic region but rare or absent in another. Collectively, these HIV-1 types may be considered to form a group, which is usually referred to as group M (major).

In 1987, a highly divergent variant of HIV-1 was isolated that was immunologically easily distinguishable from commonly encountered HIV strains (5). This variant is described in EP-0 345 375, U.S. Pat. Nos. 5,304,466, and 5,567,603. This virus (ANT70) was antigenically closer to HIV-1 reference strains than it was to HIV-2, but was nevertheless clearly very different. The sequence of the entire provirus was subsequently determined (6). While the genome organization of this virus confirmed that this isolate was an HIV-1, a comparison of its sequence with those of many other reference strains showed that this virus was highly divergent, and phylogenetic analyses placed this isolate in its own unique branch of the HIV phylogenetic tree.

In 1991, a second, highly divergent HIV-1 strain (MVP5180) was isolated and described (7). This isolate was disclosed in EP-0 591 914, and was found to cluster phylogenetically with ANT70. The genetic distance between these two isolates was approximately as great as the distance between the virus types belonging to group M. Together, these two isolates defined a new group of HIV-1 isolates. Because these isolates clustered outside the normal cluster of conventional HIV-1 isolates, they represented a new group, usually referred to as group O (outlier).

In 1992, a third person was identified in France who was infected with a group O strain (8). The sequence of the immunologically important viral env gene was determined, and is described in WO 96/12809. Subsequently, several additional group O-infected patients were identified in France (9), and the sequence of portions of the viral env proteins of these isolates was also determined. These sequences have been described in PCT/FR96/00294. An analysis of all of the available sequences showed that they cluster together in the branch of the HIV-1 phylogenetic tree corresponding to group O. Unlike group M, there seems to be little evidence for the existence of discrete virus types within the outlier group. With the exception of the French VAU isolate, virtually all of the group O isolates to date share a link to West-Central Africa. In this portion of Africa, it has been estimated that between 5% and 8% of all cases of HIV-1 infection are caused by group O variants, however, these percentages are strongly dependent on the specific geographical region (10, 11).

While there seems to be no significant differences between group M and group O strains in terms of pathology or disease progression, the detection of antibodies produced in response to a group O infection can be unreliable when the antigens used for serological testing are derived exclusively from group M strains (12, 13). Although antibodies produced to group O antigens will often cross-react with the corresponding group M antigens, the sensitivity for anti-group O antibodies can be significantly improved by incorporating a group O antigen into the test.

Although the existence of HIV-1 groups and types is well-established, an increasing number of isolates have been identified that cannot be conveniently assigned to a specific HIV-1 group M type. Through sequence analysis it has been possible to demonstrate that these isolates are the products of recombination between viruses belonging to two or more different types. In some cases, multiple recombination events must have occurred, giving rise to “mosaic” genomes. Multiple types have been shown to coexist within a single patient, and there have been reports of multiple group M types coexisting in a patient together with a group O strain (14, 15). Since the genomes of group M and group O strains also share regions which are very highly conserved, legitimate recombination could presumably occur between these viruses as well.

A preferred antigen for the detection of antibodies produced in response to HIV infection is the transmembrane portion of the viral envelope protein. This protein, referred to as gp41, is cleaved from a gp160 precursor in the infected cell by a cellular protease. This protein contains the viral fusion peptide at its N-terminus, which the virus needs in order to fuse with and penetrate a new host cell. It also provides an anchor for the surface envelope glycoprotein gp120, which is responsible for recognizing CD4 molecules and co-receptors for the virus on the surface of susceptible cells. The interaction between gp120 and gp41 is, however, non-covalent and somewhat labile. The gp41 protein is itself anchored in the viral or host cell membrane via a hydrophobic membrane-spanning region.

Little is known of the detailed three-dimensional structure of this protein. A limited amount of structural information concerning the extracellular domain of this protein is available from the Brookhaven Protein Data Base. However, the immunologically most relevant portion of gp41 is absent, probably because it is too mobile to give rise to reflections. A comparison of viral gp41 amino acid sequences corresponding to this immunologically important region reveals the presence of several extremely highly conserved amino acids in what is presumably the top of a tight disulfide-stabilized loop, suggesting that these amino acids serve an essential structural and functional role.

SUMMARY OF THE INVENTION

This invention relates to peptides, their preparation and use. Each peptide has a sequence that corresponds to the immunodominant region of the HIV-1 group O gp41 envelope protein. The sequence is characterized in that it does not correspond to any known naturally occurring group O variant.

In another aspect, this invention relates to a peptide, as described above, that is antigenic. Preferentially it binds anti-HIV-1 group O antibodies.

In yet another aspect, this invention relates to the use of the peptide, as described above, for the detection of antibodies produced in response to HIV-1 group O infection.

In yet another aspect, this invention relates to compositions and kits for determining the presence of HIV-1 group O antibodies, comprising the peptide as described above or its analog.

In yet another aspect, this invention relates to anti-HIV-1 group O antibodies and their production using the peptides, and their use in detecting HIV-1 antigens and HIV-1 infection.

A preferred peptide referred to herein as "peptide 147" comprising the following amino acid sequence:

NQQRLNSWGCKGRIICYTSARWH, (SEQ ID NO:59)

wherein the amino-terminus is at the left of the sequence. The peptide may be modified chemically (16) at either end to endow it with properties that will facilitate its use, such as N-terminal acetylation, biotinylation, or the addition of a spacer arm to provide physical distance between the peptide and a functional group used to anchor the peptide to a solid phase or a carrier.

In addition to peptide 147 several variations of the amino acid sequence of peptide 147 were found to be useful.

A preferred peptide related 147 comprises the following amino acid sequence:

XQQRLNSWGCKGRIICYTSARWH, (SEQ ID NO:60)

wherein X can be any natural amino acid other than L-asparagine or a non-natural amino acid, that is, one that is not among the 20 recognized naturally occurring amino acids; but which may occur naturally or be of human design.

Another peptide related to 147 comprises the following amino acid sequence:

ETLMQXQQRLNSWGCKGRIICYTSARWH, (SEQ ID NO:62)

wherein X denotes any natural amino acid other than L-asparagine, or a non-natural amino acid.

Each of the preferred peptides may be modified chemically at their the amino or carboxyl terminus to endow it with properties that will facilitate its use such as, but not limited to, N-terminal acetylation, biotinylation, or the addition of a spacer group to provide physical distance between the peptide and a functional group used to anchor the peptide to a solid phase or a carrier.

The invention further relates to the preparation of a mosaic. A mosaic is a recombinant group M gp41 protein in which the group M immunodominant region has been replaced by an O-like immunodominant sequence. An α-helical antigenic region located downstream from the immunodominant region was also modified in a way to increase its likelihood of being recognized by anti-group O antibodies, while still retaining those amino acids required for inter-helix interactions and structural stabilization of the protein. The resulting recombinant is therefore an artificially constructed group M/group O hybrid that does not exist in nature.

In another aspect, this invention relates to the use of a recombinant protein, as described above, for the detection of antibodies produced in response to HIV-1 group O infection.

In another aspect, this invention relates to a recombinant protein, as described above, that preferentially binds anti-HIV-1 group O antibodies.

In yet another aspect, this invention relates to compositions and kits for determining the presence of HIV-1 group O antibodies, comprising a recombinant protein as described above.

In yet another aspect, this invention relates to anti-HIV-1 group O antibodies and their production using the recombinant protein, and their use in detecting HIV-1 antigens and HIV-1 infection.

Preferred group O replacements are:

```
                                        (SEQ ID NO:64)
i)     RARLQALETLMQNQQRLNSWGCKGRIICYTSARWH,

       and

                                        (SEQ ID NO:65)
ii)    DQQVNNVSSIIYDKILEAQDQQEENVRELLELD
```

wherein the amino-terminus is at the left of the sequence.

The recombinant protein may be modified chemically at either end to endow it with properties that will facilitate its use, such as N-terminal acetylation, biotinylation, or the addition of a spacer arm to provide physical distance between the protein and a functional group used to anchor it to a solid phase or a carrier.

In yet another aspect, this invention relates to compositions and kits comprising a peptide or recombinant protein, as described above, and one or more antigens directed to other anti-HIV-1 type antibodies.

In yet another aspect, this invention relates to methods for detecting HIV-1 infection using a peptide or recombinant protein, as described above, in combination with one or more antigens directed to other HIV-1 type antibodies.

BRIEF DESCRIPTION OF THE DRAWINGS

FIG. 1. Alignment of HIV-1 group O immunodominant region amino acid sequence. (SEQ ID NO:1–30)

-continued

Figure 5A:
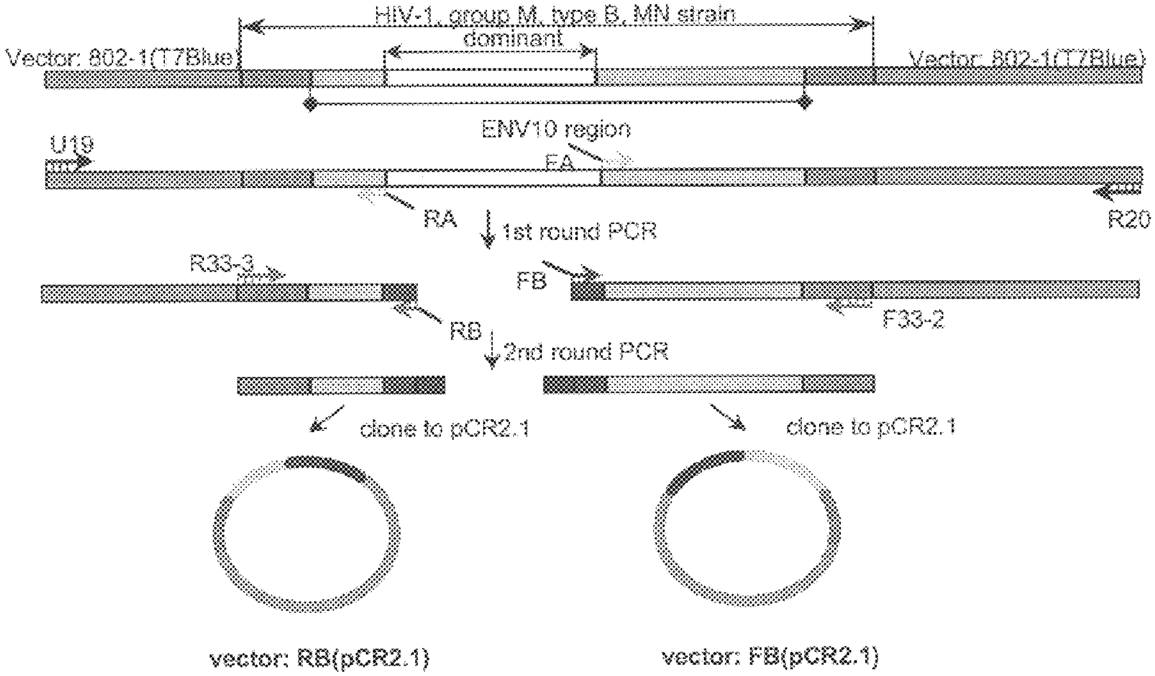

| | | |
|---|---|---|
| FIG. 2. | Recognition of peptides 147 and 80 by an HIV-1 group O sample. | |
| FIG. 3. | Ectodomain of gp41 (MN isolate) | (SEQ ID NO:70) |
| FIG. 4. | Alignment of MN (type B) and group O gp41 sequences in the region of the descending helix | (SEQ ID NO:31–45) |
| FIGS. 5 a–c. | The stepwise reconstruction and replacement of the immunodominant region using overlapping synthetic oligonucleotides. | |
| FIG. 5 d. | The nucleotide sequence of the primers used in FIGS. 3 a-c. | (SEQ ID NO:46–56) |
| FIG. 6 a | The amino acid sequence of DHFR-hENV-MH. | (SEQ ID NO:57) |
| FIG. 6 b. | The amino acid sequence of DHFR-hES-MH. | (SEQ ID NO:58) |

DETAILED DESCRIPTION OF THE INVENTION

A "sample" as used herein, refers to any substance which may contain the analyte of interest. A sample can be biological fluid, such as whole blood or whole blood components including red blood cells, white blood cells, platelets, serum and plasma, ascites, urine, cerebrospinal fluid, and other constituents of the body which may contain the analyte of interest An "antibody" as used herein may be may be monoclonal or polyclonal and may be of any species of origin, including for example, human, rat, mouse, rabbit, horse, sheep, or may be chimeric antibodies. The antibodies may be recombinant monoclonal antibodies or chemically constructed. See M. Walker et al. Molec. Immunol. 26, 403–11 (1989); U.S. Pat. Nos. 4,474,893; 4,816,567; and 4,676,980.

An "antigen" as used herein refers to any substance that as a result of coming in contact with appropriate tissues of an animal body, induces a state of sensitivity and/or resistance to infection. "Antigenic" means immunogenic or having the properties of an antigen, including but not limited to the generation of antibodies that bind the antigen. Antigens can be proteins, oligopeptides, or polypeptides and can be prepared using recombinant technology as well as synthetic methods.

For the purposes of the present invention it should be noted that because the genetic code is degenerate, more than one codon may be used to encode a particular amino acid, and therefore, the amino acid sequence can be encoded by any of a set of similar DNA oligonucleotides.

Furthermore, it is known that there is a substantial amount of redundancy in the various codons which code for specific amino acids. Therefore, this invention is also directed to those DNA sequences which contain alternative codons which code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the peptide.

As used herein, a "functional derivative" of the peptide is a compound that possesses a biological activity (either functional or structural) that is substantially similar to the biological activity of the peptide of the invention. The term "functional derivatives" is intended to include the "fragments," "variants," "degenerate variants," "analogs" and "homologues" or to "chemical derivatives" of the peptide. The term "fragment" is meant to refer to any subset of the peptide. The term "variant" is meant to refer to a molecule substantially similar in structure and function to either the entire mosaic or peptide molecule or to a fragment thereof. A molecule is "substantially similar" to the mosaic or peptide if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the entire mosaic or peptide molecule or to a fragment thereof.

Following expression of the peptide in a recombinant host cell several peptide purification procedures are available and suitable for use. For example, the peptide may be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography . In addition, recombinant peptides can be separated from other cellular proteins by use of an immunoaffinity column made with monoclonal or polyclonal antibodies specific for full length peptides, or fragments.

Examples are set forth below. The example are intended to illustrate and not limit the invention.

EXAMPLE 1

Sequences. To determine which amino acids were characteristic of group O strains, gp41 sequences from as many different isolates possible (complete and partial) were collected and aligned. Many of these sequences were available from the scientific literature, while others were determined in this laboratory. Attention was focused towards the region of gp41 known to be immunodominant and of particular diagnostic value. The sequences used for the comparison were obtained from the following sources:

TABLE 1

Sources of HIV-1 group O sequences

| Sequence | reference |
| --- | --- |
| ANT70 | 6 |
| MVP5180 | 7 |
| VAU | 8 |
| DUR | WO 96/12809 |
| POC, FAN, LOB, MAN, NAN, ESS, NKO, BCF09, BCF12, BCF13, BCF14 | PCT/FR96/00294 |
| 686 | 17 |
| ABT063, ABT124, ABT1123, ABT2156, 193Ha | 18 |
| CDC7755, CDC1897 | 19 |
| HLD28, 1515, 1516, D47-2d, HCYT2c, Nr42, PE41 | this laboratory |

Viral amino acid sequences were trimmed to a 33 amino acid-fragment containing the immunodominant region of gp41 and were aligned using the program MEGALIGN (DNAStar). The alignment is shown in FIG. 1.

The height of the column above each amino acid position shows graphically how well the amino acid in each position is conserved. Of the 33 positions in the region of interest, 18 amino acids are perfectly conserved in all strains. In the other 15 positions that are less well conserved, a closer examination of the amino acids found in these positions reveals that there is frequently a preference for amino acids with certain characteristics. For example, in positions 9 and 25, there is a strong preference for an amino acid with a hydrophobic side chain. There is also a strong preference for a lysine residue in position 21, and a positively charged amino acid in position 23.

Because it is known that the immunodominant region is primarily situated between amino acids 11 and 33 in the region shown in Table 3, a peptide sequence was derived in which an amino acid is incorporated in each position that can also be found in a naturally occurring strain. However, the resulting sequence is unique and does not correspond to that of any known group O virus. This sequence is approximately 62% identical to that of the original ANT70 isolate.

The amino acid sequence of the peptide (peptide 147) is as follows:

NQQRLNSWGCKG RI ICYTSARWH (SEQ ID NO:59)

The following sequence alignment shows the similarities and differences between this sequence and the sequence of the original ANT70 isolate:

```
ANT7O        NQQLLSLWGCKGKLVCYTSVKWN  SEQ ID NO:68)

peptide 147 NQQRLNSWGCKGRIICYTSARWH  (SEQ ID NO:59)
```

Peptide synthesis. Peptide synthesis was carried out using 9-fluorenylmethoxycarbonyl (Fmoc) chemistry on commercially available polystyrene:divinylbenzene-crosslinked resin bearing the modified Rink linker in order to generate peptides with a C-terminal amide following cleavage. Protected amino acids were activated in situ using an equimolar quantity of N-[(dimethylamino)-1H-1,2,3-triazolo[4,5-b]pyridin-1-ylmethylene]-N-methylmethanaminium hexafluorophosphate N-oxide (HATU) and 1-hydroxy-7-azabenzotriazole (HOAt), and a 2-fold molar excess of N-methylmorpholine (NMM) in N-methylpyrrolidone (NMP). A 4-fold excess of activated amino acid was used with respect to the loading capacity of the resin. Trityl (Trt) side-chain protection was used for glutamine, asparagine, cysteine, and histidine. The hydroxyl functions of serine, threonine, and tyrosine were protected with the t-butyl (tBu) group, the side chain of lysine was protected with the t-butyloxycarbonyl (tBoc) group, and 2,2,5,7,8-pentamethylchroman-6-sulfonyl (Pmc) group was used for the side chain of arginine. All other amino acids were coupled without side chain protection.

Removal of the Fmoc group at the beginning of each cycle was achieved by treating the resin-bound peptide with a mixture of 2% 1,8-diazabicyclo[5.4.0]undec-7-ene and 2% piperidine in NMP for 15 minutes.

To facilitate the binding of the peptide to the solid phase for testing, the peptide was synthesized with a biotin residue at its amino terminus. Two glycine residues were added to the N-terminus of the peptide to serve as a spacer arm before attaching the biotin. Biotin was coupled by in situ activation of its carboxyl group using an equimolar quantity of O-(benzotriazol-1-yl)-1,1,3,3-tetramethyluronium tetrafluoroborate (TBTU) and a 2-fold molar excess of NMM. The biotin was dissolved in 30% dimethylsulfoxide (DMSO), 70% NMP prior to activation.

Cleavage of the resin-bound peptide was accomplished by treating the peptide resin using a mixture of trifluoroacetic acid, phenol, thioanisole, ethanedithiol, and water (82.5:5:5:2.5:5) (reagent K). Following cleavage, the peptide-containing cleavage mixture was filtered off and the volume reduced in a rotary evaporator. Methyl-t-butylether was then added to precipitate the peptide. The precipitated crude peptide was collected by filtration, dried under vacuum, and purified by reversed phase HPLC. Fractions containing the desired product were identified by electrospray mass spectrometry, lyophilized, and stored desiccated at 4° C.

EXAMPLE 2

Serological recognition of the peptide by HIV-1 group O sera. Peptide 147 was evaluated for its ability to be recognized by anti-HIV-1 group O antibodies present in human serum from infected individuals. All group O samples were confirmed to be positive for HIV-1 group O by reverse transcriptase-polymerase chain reaction (RT-PCR) amplification of viral gp41 sequences using O-specific primers. The identity of the PCR product was further confirmed by DNA sequencing.

A preferred method for demonstrating antibody binding is the enzyme-linked immunosorbent assay (ELISA). This technique involves binding of the antigen to a solid phase, bringing the fluid to be tested into contact with the antigen-coated solid phase, washing away any unbound material, and then detecting bound antibodies with an enzyme-labeled second antibody. The presence of the enzyme is detected using a chromogenic or luminogenic substrate.

To evaluate biotinylated peptide 147, wells of a microtiter plate were coated with streptavidin at a concentration of 1 μg/ml in 50 mM carbonate buffer, pH 9.6 (200 μl/well). Excess unbound streptavidin was removed by washing several times with phosphate buffered saline (PBS). Biotinylated peptide 147 was dissolved in a minimal volume of pure DMSO and then diluted into PBS to a concentration of 0.5 μg/ml. Two hundred microliters of the peptide solution were added to each well and the peptide allowed to bind to the streptavidin. After removing unbound peptide by washing with PBS, serum samples obtained from HIV-1 group O-infected patients were added to the wells of the plate. After a suitable incubation period, unbound material was removed by washing with PBS. A dilution of an anti-lgG:horse radish peroxidase (HRP) conjugate was added to each well and incubated for 30 minutes at 37° C. Unbound material was removed by extensive washing. Substrate solution containing O-phenylenediamine (OPD) and $H_2O_2$ was added to each well and the plate was further incubated, protected from light. After a 30 minute incubation period at room temperature, the reaction was terminated by the addition of 50 μl of 4N $H_2SO_4$ and the absorbance of each well was read at 492 nm.

Peptide 147 was first tested by using undiluted (10 μl) serum samples. The results are shown in Table 2. The sample measurements are in optical density (OD).

TABLE 2

Recognition of peptide 147 using undiluted specimens.

| undiluted samples | OD492 |
|---|---|
| negative control | 0.056 |
| ODS001 | 2.500 |
| ODS002 | 2.500 |
| ODS003 | 2.500 |
| ODS004 | 2.500 |
| ODS006 | 2.500 |
| ODS007a | 2.500 |
| ODS007b | 2.500 |
| ODS009 | 2.500 |
| type B sample | 1.926 |

Samples ODS007a and b are consecutive bleeds from the same individual. The negative control sample is from an uninfected blood donor. These results show that antibodies produced in response to an HIV-1 group O infection are capable of recognizing peptide 147.

A panel of serially diluted group O sera was tested with peptide 147 in order to evaluate the sensitivity of an ELISA using this antigen. Streptavidin-coated plates were prepared and loaded with peptide 147 as before, and tested using the dilutional panels. In addition, in order to compare the performance of peptide 147 with that of a genuine group O sequence, a second peptide was synthesized (peptide 146) corresponding to the sequence of the DUR variant.

These peptides cover precisely the same region of gp41, and were tested in parallel. These results are shown in Table 3:

| | | dilution of | $OD_{492}$ | |
|---|---|---|---|---|
| Panel | Sample | original sample | peptide 147 | peptide 146 |
| OP1 | OP1A | 2 | 2.500 | 1.732 |
| | OP1B | 4 | 2.298 | 0.563 |
| | OP1C | 8 | 2.465 | 1.481 |
| | OP1D | 16 | 2.387 | 1.186 |
| | OP1E | 32 | 2.013 | 0.978 |
| | OP1F | 64 | 1.448 | 0.356 |
| | OP1G | 128 | 1.150 | 0.432 |
| | OP1H | 256 | 0.927 | 0.258 |
| | OP1I | 512 | 0.504 | 0.123 |
| | OP1J | 1024 | 0.053 | 0.015 |
| OP2 | OP2A | 5 | 2.236 | 1.831 |
| | OP2B | 10 | 2.320 | 1.822 |
| | OP2C | 20 | 2.157 | 1.142 |
| | OP2D | 40 | 1.844 | 0.775 |
| | OP2E | 80 | 1.061 | 0.613 |
| | OP2F | 160 | 0.689 | 0.104 |
| | OP2G | 320 | 0.327 | 0.076 |
| | OP2H | 640 | 0.184 | 0.060 |
| | OP2I | 1280 | 0.179 | 0.041 |
| | OP2J | 2560 | 0.090 | 0.045 |
| OP3 | OP3A | 300 | 0.229 | 0.334 |

-continued

| | | dilution of | $OD_{492}$ | |
|---|---|---|---|---|
| Panel | Sample | original sample | peptide 147 | peptide 146 |
| | OP3B | 600 | 0.373 | 0.334 |
| | OP3C | 1200 | 0.211 | 0.132 |
| OP4 | OP4A | 100 | 0.774 | 1.220 |
| | OP4B | 200 | 0.608 | 0.726 |
| | OP4C | 400 | 0.398 | 0.608 |
| | OP4D | 800 | 0.277 | 0.430 |
| | OP4E | 1600 | 0.040 | 0.051 |
| OP5 | OP5A | 100 | 1.624 | 1.100 |
| | OP5B | 200 | 1.027 | 0.74 |
| | OP5C | 400 | 0.225 | 0.205 |
| | OP5D | 800 | 0.302 | 0.264 |
| OP6 | OP6A | 50 | 0.667 | 1.905 |
| OP7-2 | OP7-2A | 100 | 2.081 | 2.302 |
| | OP7-2B | 200 | 1.817 | 2.104 |
| | OP7-2C | 400 | 1.346 | 1.568 |
| | OP7-2D | 800 | 0.847 | 0.935 |

Table 3. Sensitivity of antibody detection using peptide 147.

These results demonstrate that even with highly diluted samples, peptide 147 is a suitable antigen capable of binding antibodies against the group O gp41 immunodominant region. With a number of the panels, the performance of peptide 147 equaled or significantly exceeded that of a genuine group O sequence.

To compare the performance of peptide 147 to another genuine group O sequence, the peptide corresponding to the ANT70 sequence was synthesized (peptide 80). Peptides 147 and 80 were dissolved at the same concentration, serially diluted, and bound to streptavidin-coated wells. A 1:60 dilution of serum sample ODS007b (see Table 3) was added to all wells and incubated. After washing, an anti-human lgG:HRP conjugate was added, incubated, and the wells again thoroughly washed. In this case, a chemiluminescent substrate was used, consisting of luminol and a peracid salt. The emitted light was quantified using a luminometer. The results are tabulated in Table 4 and shown graphically in FIG. 2.

TABLE 4

Comparison of antibody recognition of peptides 147 and 80.

| | luminescent units | |
|---|---|---|
| peptide (ug/ml) | peptide 147 | peptide 80 |
| 2.500 | 2.374 | 1.821 |
| 1.250 | 2.885 | 2.908 |
| 0.625 | 3.093 | 2.854 |
| 0.313 | 2.090 | 2.294 |
| 0.156 | 1.199 | 1.288 |
| 0.078 | 0.740 | 0.621 |
| 0.039 | 0.504 | 0.376 |
| 0.020 | 0.619 | 0.387 |

These results demonstrate that the amino acid sequence of peptide 147 is comparable to that of a naturally occurring isolate for the detection of antibodies to HIV-1 group O.

EXAMPLE 3

Antibody recognition of variants of peptide 147:

The following two peptides were synthesized:

Peptide 147-4:

EQQRLNSWGCKGRIICYTSARWH (SEQ ID NO:61)

Peptide 147-5:

GRETLMQDQQRLNSWGCKGRIICYTSARWH (SEQ ID NO:63)

In peptide 147-5, the N-terminal glycine was added to function as a spacer group, while the arginine in position 2 was added to enhance the solubility of the peptide in aqueous buffers. Both of these peptides were evaluated for their ability to be recognized by HIV-1 group O serum samples in an antibody capture format. In general, in such an assay, a peptide is bound to a solid phase and bivalent antibody presents in a sample binds to the peptide linked thereto. Bound antibody is subsequently detected using a conjugate made of the peptide in question coupled to horse-radish peroxidase. The peptide-HRP conjugate binds to antibody which in turn is bound to the solid phase linked peptide. Methods suitable for preparing such conjugates may be found readily in the scientific literature and are well known to those versed in the art.

Microwell plates were pre-coated with either peptide 147-4 or 147-5. A dilution of a serum sample was then incubated for 1 hour at 37° C., after which the plate was washed extensively. A 1:100 dilution of either peptide 147-4 or 147-5 conjugated to HRP was then added and allowed to incubate for an additional hour at 37° C. Following this incubation, the plates were again thoroughly washed. The presence of bound conjugate was detected by addition of substrate for HRP (O-phenylenediamine) and $H_2O_2$. Antibody recognition of peptides 147-4 and 147-5 is shown in Table 5 below.

TABLE 5

Antibody recognition of peptides 147-4 and 147-5

| sample (dilution) | Optical Density $(OD)_{492}$ peptide 147-4 Ag peptide 147-4 conjugate | peptide 147-5 Ag peptide 147-5 conjugate |
|---|---|---|
| negative control | 0.010 | 0.022 |
| ODS001 (1:200) | >2.500 | >2.500 |
| ODS002 (1:175) | 0.785 | 1.343 |
| ODS006 (1:100) | 0.133 | 0.266 |
| ODS007 (1:1,500) | 0.241 | 0.316 |

The peptides were evaluated for their ability to be recognized by anti-HIV-1 group O antibodies present in human serum from infected individuals. All group O samples were confirmed to be positive for HIV-1 group O by reverse transcriptase-polymerase chain reaction (RT-PCR) amplification of viral gp41 sequences using O-specific primers. The identity of the PCR product was further confirmed by DNA sequencing.

The results presented in the table demonstrate that the noted sequence variations of peptide 147 are suitable for detecting the presence of antibodies produced in response to an HIV-1 group O infection, even when the serum samples are highly diluted. The results also indicate that the use of the longer peptide results in a somewhat higher signal than the shorter version.

It is possible to introduced variations to the basic amino acid sequence of peptide 147 and retain the ability to detect antibodies produced in response to infection by HIV-1 group O.

EXAMPLE 4

Design of a recombinant antigen for antibody detection. In many cases, larger proteins often function better than short peptides for the detection of antibodies because they are able to present discontinuous epitopes created by the juxtaposition of distant regions of the polypeptide chain in the native protein. Other advantages to using recombinant proteins include the ability to incorporate into the protein specific sequences unrelated to the actual antigen in order to facilitate purification of the protein, binding to the solid phase, or to provide the protein with other desirable characteristics.

The sequence of the group M HIV-1 type B isolate MN was used as a point of departure in designing a novel antigen with desirable characteristics for the detection of anti-group O antibodies. The env gene product is a polypeptide 855 amino acids in length. Cleavage of the gp160 precursor occurs between amino acids 513 and 514 to give rise to the envelope proteins gp120 and gp41 found in mature virions. Of particular interest for antibody detection is the ectodomain of gp41, shown in FIG. 3.

The design of a new recombinant protein should take into account any available structural information to avoid creating a protein that is intrinsically hindered in its ability to re-form its native structure in solution. The structures 1AIK and 1ENV were obtained from the Brookhaven Protein Database and viewed using the programs Rasmol and Swiss-Model. These crystallographic structures show the presence of two interacting helices which form a coiled coil. The sequences connecting these two helices in the 1ENV structure (and which encompass the immunodominant region) are absent, suggesting that the interconnecting region comprising the immunogenic region at the top of a loop is too mobile to generate reflections. The helices for which there is crystallographic data are indicated in FIG. 3. The N- and C-terminal limits to each helix are the limits for which crystallographic data is available; they are not necessarily the true boundaries of these helices in the native gp41 protein.

The potential importance of sequences contained within the "descending" helix shown in FIG. 3 has been demonstrated for group O sera and are described in WO 95/32293. To determine which amino acids in the MN sequence should not be mutated, the available 3-dimensional structures were examined to identify those amino acids likely to be involved in stabilizing the interactions between the two helices. The following close contacts were identified:

G548→N657

Q551→Q653

Q552→Q654

A562→I643

H565→Y639

L569→I636

W572→W632

W572→W629

An examination of available sequences in the HIV Sequence Data Base maintained by the Los Alamos National Laboratory reveals that many of these amino acids are highly conserved. Mutations, when present, often have similar characteristics, such as a hydrophobic side-chain or a side-chain with the ability to participate in hydrogen bonding. The sequence of the MN isolate in the region of the descending helix (amino acids 633–665) was aligned and compared to that of all group O strains for which sequence information is available. This alignment is shown in FIG. 4.

FIG. 4 also shows which amino acids in this region are conserved, even between the type B sequence and the group O sequences. This sequence comparison suggests very strongly that there is a high degree of structural homology between group M and group O strains.

To arrive at a sequence representative of group O, only the group O sequences were considered. The sequence chosen after evaluation of the amino acids found in each position is as follows:

DQQVNNVSSIIYDKILEAQDQQEENVRELLELD (SEQ ID NO:65)

This sequence has 57.6% identity to the corresponding ANT70 sequence.

Additionally, the peptide 147 group O-like immunodominant region was extended in the N-terminal direction. This larger immunodominant region has the following sequence:

RARLQALETLMQNQQRLNSWGCKGRIICYTSARWH (SEQ ID NO:64)

With the N-terminal extension, this new sequence has 68.6% identity with the original ANT70 strain.

It would be understood by one skilled in the art that a diagnostic test could be developed using either the peptides or derivatives thereof as described herein to detect antibodies found in an infected patient, or using antibodies raised against the aforementioned peptides to detect antigen found in an infected patient.

EXAMPLE 5

Construction of a "mosaic" group M/group O recombinant antigen. Having taken structural features of gp41 into account and knowing that the sequence contained within peptide 147 is suitable for the detection of anti-group O antibodies, the construction of a mosaic recombinant was undertaken. The objective was to use the MN gp41 sequence as a point of departure and substitute the two group O regions described above, thereby creating a group O antigen using the type B MN sequence as a carrier for the immunologically important domains.

Figure 5B:
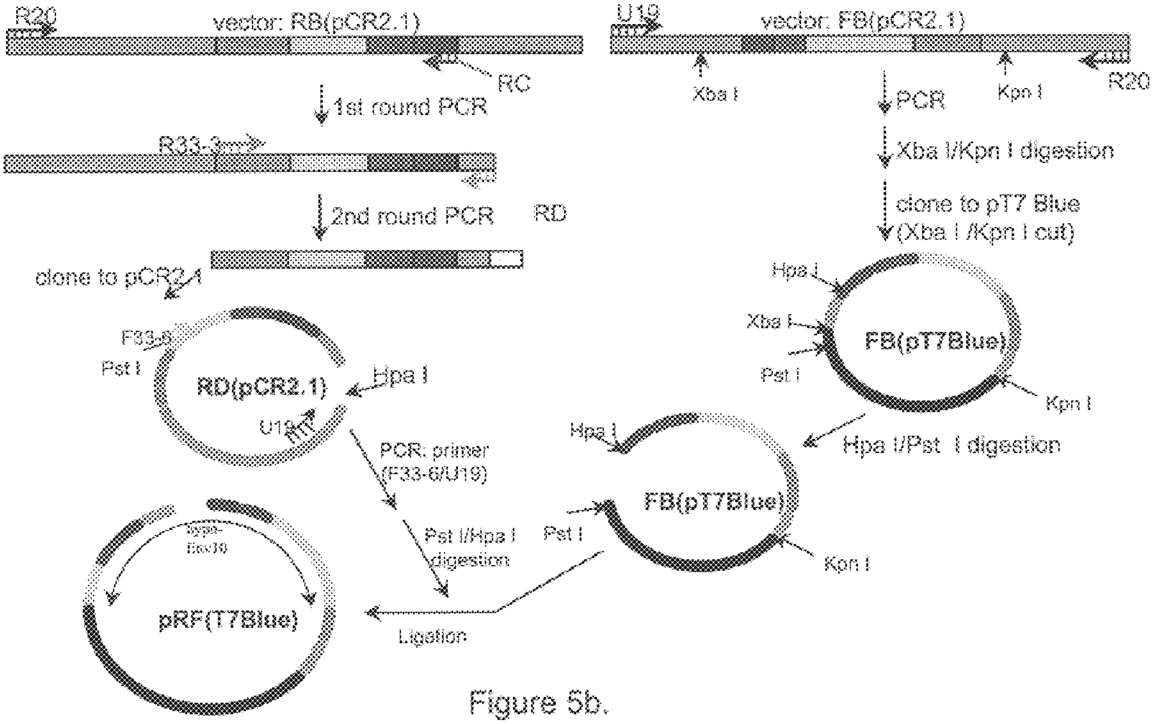
Figure 5C:
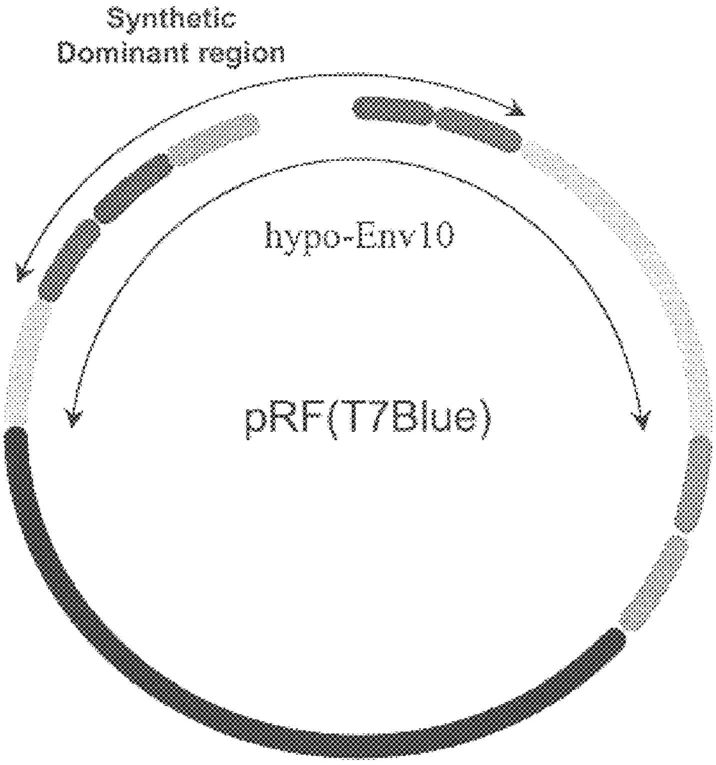

The strategy for constructing such a recombinant is shown in FIGS. 5*a–c*. The stepwise reconstruction and replacement of the immunodominant region using overlapping synthetic oligonucleotides is illustrated, along with all important restriction enzyme cleavage sites.

The sequences of the primers used are given in FIG. 5*d.*

Two constructs were made as dihydrofolate reductase (DHFR) fusion proteins. Neither of the constructs represents a full-length gp41 molecule, however, the longer of the two (DHFR-hENV-MH) contains essentially the entire ectodomain of gp41 except for the N-terminal fusion peptide. The construct DHFR-hES-MH is a truncated version of the longer fusion protein. The amino acid sequences of these fusion proteins are shown in FIG. 6, *a.* and *b.*

A C-terminal sequence derived from the myc gene was added to facilitate analysis, and a $his_6$ tail was added to facilitate purification. All non-HIV sequences are shown in boxes. The group O-like sequences are underlined.

All other sequences in the HIV portion of this recombinant are group are group M-derived.

The expression of both proteins was attempted in *Escherichia coli.* The greatest level of expression was observed for the truncated construct DHFR-hES-MH and the expressed recombinant protein was found in inclusion bodies. The cells were lysed, and the inclusion bodies harvested by well known methods. The protein was subsequently solubilized by treatment with sodium dodecyl sulfate (SDS) and dithiothreitol, and analyzed by polyacrylamide gel electrophoresis in the presence of SDS. A band was observed having the expected molecular size and was estimated to constitute about 90% of the total protein in the crude antigen preparation.

EXAMPLE 6

Performance of group M/group O "mosaic" constructs for group O antibody detection. The protein expressed as described was coated at a concentration of 0.5 μg/ml into the wells of microtiter plates for evaluation. Following coating of the protein, any remaining binding sites on the plastic were block with bovine serum albumin. Dilutions of group O sera were then tested for their ability to recognize the recombinant antigen. Bound antibodies were detected by incubation with HRP-labeled mouse anti-human IgG conjugate, and the bound conjugate was subsequently detected by addition of OPD and $H_2O_2$. The results are shown in Table 6. Table 6:

| | $OD_{492}$ | |
|---|---|---|
| Sample | wild type | DHFR-hES-MH |
| neg. control 1 | 0.186 | −0.061 |
| ODS001 | 0.056 | 1.179 |
| ODS002 | 1.209 | 1.323 |
| type B sample | 1.579 | 0.685 |

Because these antigens were derived by taking into consideration a reasonably large number of HIV-1 group O sequences, the new sequences are thought to better represent the spectrum of group O variants which are likely to occur in nature and may therefore have a broader specificity for the detection of anti-group O antibodies. Experimental results show that these antigens function as well, and in some cases better, than naturally occurring viral sequences for the detection of antibodies generated in response to HIV-1 group O infections.

The use of "mosaic" recombinants offer advantages in that they display the desired antigenic determinants but can be more easily bound by direct coating to a solid phase than peptides for use in an immunoassay. Furthermore, the recombinants, because of their increased length and more stabilized structure relative to peptides, present the determinants more accurately.

All cited materials herein are hereby incorporated by reference. Accordingly, it should be noted that the present invention includes all modifications falling within the scope of the following claims.

Literature Cited

1. Barré-Sinoussi, F., et al., *Science* (1983) 220:868–871.
2. Clavel, F., et al., *Science* (1986) 233:343–346.
3. Goodenow, M., et al., *J. Acquir. Immun. Defic. Syndr.* (1989) 2:344–352.
4. Leitner, T., et al., *Human Retroviruses and AIDS Compendium* 1997 (1998), part III, pp.19–24.
5. DeLeys, R., et al., *J. Virol.* (1990) 64:1207–1216.
6. Vanden Haesevelde, M., et al., *J. Virol.* (1994) 68:1586–1596.
7. Gürtler, L. G., et al., *J. Virol.* (1994) 68:1581–1585.
8. Charneau, P., et al., *Virology* (1994) 205:247–253.
9. Loussert-Ajaka, I., et al., *J. Virol.* (1995) 69:5640–5649.
10. Mauclère, P., et al., *AIDS* (1997) 11:445–453.
11. Peeters, M., et al., *AIDS* (1997) 11:493–498.
12. Loussert-Ajaka, I., et al., *Lancet* (1994) 343:1393–1394.

13. Britvan, L., et al., *MMWR* (1996) 45:561–565.
14. Heyndrickx, L., et al., *Lancet* (1996) 347:902–903.
15. Takehisa, J., et al., *J. Acquir. Immun. Defic. Syndr.* (1997) 14:81–82.
16. Hermanson, G. T.; *Bioconjugate Techniques*, Academic Press, San Diego, U.S.A., 1996.
17. Delaporte, E., et al., *AIDS* (1996) 10:903–910.
18. Brennan, C., et al., *AIDS Res. Human. Retrovir.* (1997) 13:901–904.
19. Hackett, J., et al., *Fourth Conf. on Retroviruses and Opportun. Infect., Washington, D.C.* (1997), abstr. 160.

---

We claim:

1. A peptide comprising an amino acid sequence selected from the group consisting of

SEQ ID NO:59
NQQRLNSWGCKGRIICYTSARWH,

SEQ ID NO;61
EQQRLNSWGCKGRIICYTSARWH,

SEQ ID NO:69
GRETLMQDQQRLNSWGCKGRIICYTSARWH,

SEQ ID NO:60
XQQRLNSWGCKGRIICYTSARWH,

-continued

SEQ ID NO:62
ETLMQXQQRLNSWGCKGRIICYTSARWH,

SEQ ID NO:64
RARLQALETLMQNQQRLNSWGCKGRIICYTSARWH, and

SEQ ID NO:65
DQQVNNVSSIIYDKILEAQDQQEENVRELLELD.

2. The peptide of claim 1 wherein said peptide binds anti-HIV group O antibodies.

3. The peptide of claim 1 wherein said peptide is made by recombinant or synthetic chemistry methods.

* * * * *